US010941380B2

(12) United States Patent
Hofmeister et al.

(10) Patent No.: US 10,941,380 B2
(45) Date of Patent: Mar. 9, 2021

(54) BIOMIMETIC CELL CULTURE SUBSTRATES

(71) Applicant: Ultra Small Fibers, LLC, Wartrace, TN (US)

(72) Inventors: William Hudson Hofmeister, Nashville, TN (US); Lucas Hofmeister, Wuppertal (DE); Alexander Yuryevich Terekhov, Estill Springs, TN (US); Jose Lino Vasconcelos da Costa, Murfreesboro, TN (US)

(73) Assignee: Ultra Small Fibers, LLC, Wartrace, TN (US)

( * ) Notice: Subject to any disclaimer, the term of this patent is extended or adjusted under 35 U.S.C. 154(b) by 0 days.

(21) Appl. No.: 15/014,762

(22) Filed: Feb. 3, 2016

(65) Prior Publication Data

US 2016/0222345 A1    Aug. 4, 2016

Related U.S. Application Data

(60) Provisional application No. 62/111,551, filed on Feb. 3, 2015.

(51) Int. Cl.
*C12N 5/00* (2006.01)
*B29C 67/20* (2006.01)
*B29K 67/00* (2006.01)
*B29K 105/00* (2006.01)

(52) U.S. Cl.
CPC ............ *C12N 5/0068* (2013.01); *B29C 67/20* (2013.01); *B29K 2067/04* (2013.01); *B29K 2105/256* (2013.01); *C12N 2533/30* (2013.01); *C12N 2535/10* (2013.01)

(58) Field of Classification Search
CPC ................ B29C 67/20; B29K 2067/04; B29K 2105/256; C12N 2533/30; C12N 2535/10; C12N 5/0068
USPC .......................................... 428/141; 264/400
See application file for complete search history.

(56) References Cited

U.S. PATENT DOCUMENTS

| 2013/0204392 | A1* | 8/2013 | Law | A61K 35/32 |
| | | | | 623/23.72 |
| 2013/0216779 | A1* | 8/2013 | Hofmeister | B82Y 40/00 |
| | | | | 428/141 |
| 2015/0093550 | A1 | 4/2015 | Hofmeister et al. | |
| 2016/0354515 | A1* | 12/2016 | Arinzeh | A61L 27/16 |

OTHER PUBLICATIONS

Albelda SM, et al., "Molecular and Cellular Properties of Pecam-1 (Endocam/Cd31)—a Novel Vascular Cell Cell-Adhesion Molecule," J Cell Biol., vol. 114, pp. 1059-1068, 1991.

Bara JJ et al., "Concise review: Bone marrow-derived mesenchymal stem cells change phenotype following in vitro culture . . . ," Stem Cells., vol. 32, pp. 1713-1723, 2014.
Barcellos-Hoff MH et al., "Functional differentiation and alveolar morphogenesis of primary mammary cultures on . . . " Development, vol. 105, pp. 223-235, 1989.
Bartosh TJ et al., "Aggregation of human mesenchymal stromal cells (MSCs) into 3D spheroids enhances their . . . ," Proc Natl Acad Sci USA, vol. 107, pp. 13724-13729, 2010.
Bhuyan MK et al., "High aspect ratio nanochannel machining using single shot femtosecond Bessel beams," Appl Phys Lett. vol. 97, p. 081102, 2010.
Chou CL et al., "Micrometer Scale Guidance of Mesenchymal Stem Cells to Form Structurally Oriented Cartilage . . . " Tissue Eng Pt A. vol. 19, pp. 1081-1090, 2013.
Courvoisier F, et al, "Surface nanoprocessing with nondiffracting femtosecond Bessel beams," Opt Lett. vol. 34, pp. 3163-3165, 2009.
Deans RJ and Moseley AB, "Mesenchymal stem cells: Biology and potential clinical uses," Exp Hematol. vol. 28, pp. 875-884, 2000.
Delobelle B et al., "A detailed study through the focal region of near-threshold single-shot femtosecond laser ablation . . . ," Opt Commun. vol. 284, pp. 5746-5757, 2011.
Dubey N et al., "Neuronal contact guidance in magnetically aligned fibrin gels: effect of variation in gel mechano- . . . ," Biomaterials, vol. 22, pp. 1065-1075, 2001.
Engler AJ et al., "Matrix elasticity directs stem cell lineage specification," Cell, vol. 126, pp. 677-689, 2006.
Foster CS et al., "Human mammary gland morphogenesis in vitro: the growth and differentiation of normal breast epitheliumin collagen . . . " Dev Biol., vol. 96, pp. 197-216, 1983.
Guvendiren M and Burdick JA, "Engineering synthetic hydrogel microenvironments to instruct stem cells," Curr Opin Biotechnol., vol. 24, pp. 841-846, 2013.
Heidemann SR and Wirtz D, "Towards a regional approach to cell mechanics," Trends Cell Biol., vol. 14, pp. 160-166, 2004.
Herbstman JF and Hunt AJ, "High-aspect ratio nanochannel formation by single femtosecond laser pulses," Opt Express, vol. 18, pp. 16840-16848, 2010.
Hockemeyer K et al., "Engineered three-dimensional microfluidic device for interrogating cell-cell interactions . . . ," Biomicrofluidics, vol. 8, p. 044105.

(Continued)

*Primary Examiner* — Janet L Epps-Smith
(74) *Attorney, Agent, or Firm* — Eric B. Fugett; Mark A. Pitchford; Pitchford Fugett, PLLC

(57) ABSTRACT

Embodiments of the presently disclosed subject matter provide biomimetic cell culture substrates comprising highly tunable patterned polymer nanofiber matrices capable of modulating expression of critical self-renewal factors and markers of cell-cell interaction to maintain stemness of human mesenchymal stem cells in vitro. Embodiments of the presently-disclosed subject matter also provide scalable, highly repeatable methods of making biomimetic cell culture substrates by hot pressing thermoplastic polymer films into femtosecond laser-ablated nanopore molds to form patterned polymer nanofiber matrices on flat thermoplastic substrates.

1 Claim, 12 Drawing Sheets

Specification includes a Sequence Listing.

(56) References Cited

OTHER PUBLICATIONS

Hosseinkhani H, et al., "Engineering three-dimensional collagen-IKVAV matrix to mimic neural microenvironment," ACS Chem Neurosci., vol. 4, 1229-1235, 2013.
Jahani H et al., "Controlled surface morphology and hydrophilicity of polycaprolactone toward selective . . . ," J Biomed Mater Res A, vol. 103, pp. 1875-1881, 2015.
Kinney MA and McDevitt TC, "Emerging strategies for spatiotemporal control of stem cell fate and morphogenesis," Trends Biotechnol., vol. 31, pp. 78-84, 2013.
Kumar S, "Cellular mechanotransduction: stiffness does matter," Nat Mater., vol. 13, 918-920, 2014.
Lindstrom S, et al., "Nanoporous Titania Coating of Microwell Chips for Stem Cell Culture and Analysis," J Biomech Sci Eng. 2010;5(3)272-79.
Londono C et al., "Nonautonomous contact guidance signaling during collective cell migration," Proc Natl Acad Sci USA, vol. 111, pp. 1807-1812, 2014.
McCall AS, et al., "Bromine Is an Essential Trace Element for Assembly of Collagen IV Scaffolds in Tissue Development and Architecture," Cell, vol. 157, 1380-1392, 2014.
McMurray RJ, et al., "Nanoscale surfaces for the long-term maintenance of mesenchymal stem cell phenotype and multipotency," Nat Mater, vol. 10, pp. 637-644, 2011.
Miroshnikova YA, et al., "Engineering strategies to recapitulate epithelial morphogenesis within synthetic three-dimensional . . . ," Phys Biol., vol. 82 p. 026013, 2011.
Mitsui K, et al., "The homeoprotein Nanog is required for maintenance of pluripotency in mouse epiblast and ES cells," Cell, vol. 113, pp. 631-642, 2003.
Murphy WL, et al., "Materials as stem cell regulators," Nat Mater., vol. 13, pp. 547-557, 2014.
Nikkhah M, et al., "Engineering microscale topographies to control the cell-substrate interface," Biomaterials, vol. 33, pp. 5230-5246, 2012.
Paszek MJ, et al., "Tensional homeostasis and the malignant phenotype," Cancer Cell, vol. 8, pp. 241-254, 2005.
Pathak A and Kumar S, "Biophysical regulation of tumor cell invasion: moving beyond matrix stiffness," Integr Biol (Camb), vol. 3, pp. 267-278, 2011.
Mohan N, et al., "Growth factor-mediated effects on chondrogenic differentiation of mesenchymal stem cells in 3D . . . ," J Biomed Mater. Res. A., vol. 94, pp. 146-159, 2010.
Pelham Jr RJ and Wang Y, "Cell locomotion and focal adhesions are regulated by substrate flexibility," Proc Natl Acad Sci USA, vol. 94, pp. 13661-13665, 1997.
Rajput D, et al., "Solution-Cast High-Aspect-Ratio Polymer Structures from Direct-Write Templates," Acs Appl Mater Inter., vol. 5, pp. 1-5, 2013.
Roeder BA, et al., "Tensile mechanical properties of three-dimensional type I collagen extracellular matrices . . . ," J Biomech Eng., vol. 124, pp. 214-222, 2002.
Sart S, et al., Three-Dimensional Aggregates of Mesenchymal Stem Cells: Cellular Mechanisms, Biological Properties, and Applications. Tissue Eng. Part B, Reviews. 2013.
Tanabe S, "Origin of cells and network information," World J Stem Cells, vol. 7, pp. 535-540, 2015.
Tibbitt MW, et al., "Hydrogels as extracellular matrix mimics for 3D cell culture," Biotechnol Bioeng., vol. 103, pp. 655-663, 2009.
White YV, et al., "Single-pulse ultrafast-laser machining of high aspect nano-holes at the surface of SiO2," Opt Express., vol. 16, pp. 14411-14420, 2008.
Xue D, et al., "Osteochondral repair using porous poly(lactide-co-glycolide)/nano-hydroxyapatite hybrid scaffolds with . . . ," J Biomed Mater Res A, vol. 94, pp. 259-270, 2010.
Yu X, et al., "Integrin alpha 2 beta 1-dependent EGF receptor activation at cell-cell contact sites," J Cell Sci., vol. 113, 2139-2147, 2000.

\* cited by examiner

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Nanog forward primer

<400> SEQUENCE: 1
aatacctcag cctccagcag atg                                              23

<210> SEQ ID NO 2
<211> LENGTH: 24
<212> TYPE: DNA
<213> ORGANISM: Artificial Sequence
<220> FEATURE:
<223> OTHER INFORMATION: Nanog reverse primer

<400> SEQUENCE: 2
tgcgtcacac cattgctatt cttc                                             24

<210> SEQ ID NO 3
<211> LENGTH: 22
<212> TYPE: DNA
<213> ORGANISM: Artificial Sequence
<220> FEATURE:
<223> OTHER INFORMATION: OCT4A forward primer

<400> SEQUENCE: 3
ccttcgcaag ccctcatttc ac                                               22

<210> SEQ ID NO 4
<211> LENGTH: 20
<212> TYPE: DNA
<213> ORGANISM: Artificial Sequence
<220> FEATURE:
<223> OTHER INFORMATION: OCT4A reverse primer

<400> SEQUENCE: 4
ggaagcttag ccaggtccga                                                  20

<210> SEQ ID NO 5
<211> LENGTH: 20
<212> TYPE: DNA
<213> ORGANISM: Artificial Sequence
<220> FEATURE:
<223> OTHER INFORMATION: ITGA2 forward primer

<400> SEQUENCE: 5
ttagcgctca gtcaaggcat                                                  20

<210> SEQ ID NO 6
<211> LENGTH: 20
<212> TYPE: DNA
<213> ORGANISM: Artificial Sequence
<220> FEATURE:
<223> OTHER INFORMATION: ITGA2 reverse primer

<400> SEQUENCE: 6
cggttctcag gaaagccact                                                  20

<210> SEQ ID NO 7
<211> LENGTH: 20
<212> TYPE: DNA
<213> ORGANISM: Artificial Sequence

```
<220> FEATURE:
<223> OTHER INFORMATION: PECAM forward primer

<400> SEQUENCE: 7
ccaagcccga actggaatct                                           20

<210> SEQ ID NO 8
<211> LENGTH: 20
<212> TYPE: DNA
<213> ORGANISM: Artificial Sequence
<220> FEATURE:
<223> OTHER INFORMATION: PECAM reverse primer

<400> SEQUENCE: 8
cactgtccga ctttgaggct                                           20

<210> SEQ ID NO 9
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 9
gcaccgtcaa ggctgagaac                                           20

<210> SEQ ID NO 10
<211> LENGTH: 19
<212> TYPE: DNA
<213> ORGANISM: Artificial Sequence
<220> FEATURE:
<223> OTHER INFORMATION: GAPDH reverse primer

<400> SEQUENCE: 10
tggtgaagac gccagtgga                                            19
```

BIOMIMETIC CELL CULTURE SUBSTRATES

CROSS-REFERENCES TO RELATED APPLICATIONS

This application claims priority to U.S. Provisional Patent Application Ser. No. 62/111,551 entitled PATTERNED NANOFIBRE MATRIX PROMOTES STEMNESS AND CELL-CELL INTERACTION OF ADULT STEM CELLS, filed Feb. 3, 2015, the entire disclosure of which is hereby incorporated herein by this reference.

STATEMENT REGARDING FEDERALLY SPONSORED RESEARCH OR DEVELOPMENT

Subject matter described herein was made with government support under Grant Numbers HL091465 and 1UH2 TR000491 awarded by the National Institutes of Health and Grant Number CAREER CBET 1056046 awarded by the National Science Foundation. The government has certain rights in the subject matter disclosed herein.

REFERENCE TO SEQUENCE LISTING OR COMPUTER PROGRAM LISTING APPENDIX

The Sequence Listing associated with this application is filed in electronic format via EFS-Web and hereby incorporated by reference into the specification in its entirety. The name of the text file containing the Sequence Listing is Sequence List 028596.55271. The size of the file is 2.10 KB, and the text file was created on Mar. 14, 2016.

TECHNICAL FIELD

The present disclosure relates generally to cell culture substrates and more specifically to tunable arrays of patterned polymer nanofiber matrices that promote stemness and cell-cell interactions in stem cells cultured on or recruited thereto.

BACKGROUND OF THE INVENTION

The ability to manipulate expansion and differentiation of stem cells has been on the forefront of materials research for several decades. However, many synthetic culture substrates resulting from these research efforts embody properties that are not completely biomimetic. In response, the biomaterials community has been reorienting their design process towards generating an optimal stem cell culture substrate that can reliably and reproducibly mimic the extracellular matrix ("ECM"), one of the primary environmental constituents that heavily influences cell behavior [1].

Generally, altered mechanical and chemical properties of cell substrates have been shown to alter tissue homeostasis, stem cell differentiation, and metastasis, as examples [2]. All of these physiological responses are initiated by "outside-in" signaling, where physical cues regulate cell function. For stem cells, and human mesenchymal stem cells ("hMSCs") in particular, design parameters for improved in vitro culture systems can heavily influence their decision to either maintain their stem cell phenotype or differentiate towards a specified cell lineage.

Guided by physical cues incorporated into the substrate design, numerous example culture systems have been and continue to be explored for diverse cell culture purposes. Poly(ε-caprolactone) ("PCL"), a common synthetic polymer used in biomedical applications, has been shown to help push hMSCs towards neural lineages when the material's hydrophobic nature is coupled with soluble factor neuralinduction media [3]. Synthetic copolymers, such as poly(vinyl alcohol)-PCL, create 3D structures reminiscent of native tissues and when loaded with growth factors have promoted hMSC differentiation into chondrocytes, thereby generating structurally robust cartilage tissue [4]. Combining polymers with metals and minerals have also shown promise in encouraging MSCs to create complex layered tissue structures such as bone-cartilage interfaces [5] in addition to providing templates to investigate MSC responses to high-throughput chemical screening protocols [6]. Finally, natural polymers like collagen have also been modified with peptides to encourage better tissue regeneration by jump-starting growth responses in slow proliferating cells like dorsal root ganglion cells [7].

Considering the importance of both cell-cell and cell-matrix adhesion molecule interactions in maintaining hMSC stemness [8-11], it is clear that flat substrates like tissue culture polystyrene ("TCPS") cannot fully recapitulate the native hMSC environment (e.g., bone marrow) that balances these two types of binding events. As a result, mechanisms of self-organization, endogenous matrix deposition, differentiation, and remodeling that encompass the traditional hMSC phenotype are disturbed [12]. Additionally, the minimal flexibility of modifying cell-adhesive surfaces of existing mass-produced culture platforms complicates the ability to probe and understand stem cell behavior as it relates to developmental and regenerative processes [13-14]. This obstacle has, thus, spurred the recent explosion in the use of gel culture systems such as polyacrylamide hydrogels [15-18], collagen hydrogels [19, 20], and MATRIGEL® [21].

Despite the contributions made by the research community, these materials do have limitations. First, it is difficult to uncouple gel properties, which limits the ability to engineer controlled cellular responses to isolated stimuli. For example, changing pore size alters gel rigidity and fiber architecture that may result in substrate properties unrepresentative of native hMSC-containing tissues [22]. Chemical transport is also inhibited across the boundary of the gel, which could produce shortfalls of chemokines and similar molecules that help hMSCs maintain their naïve phenotypes [23]. Furthermore, batch-to-batch inconsistency can obfuscate fundamental mechanisms being studied that pertain to hMSC homeostasis [24].

Given the challenges with gel systems, other research groups have turned to electrospinning as another potential approach to generate synthetic cell culture models [25]. However, electrospinning is limited by the challenges of variations in fiber morphology and internal void structure due to the complexity of the fabrication process. Hence, with all the aforementioned shortfalls of existing biomaterials approaches, the development of scalable and physiologically relevant biomimetic culture models that mimic hMSC niches to maintain stemness in vitro remains a top priority as very few studies have been able to design culture templates that successfully achieve this goal [26].

BRIEF SUMMARY OF THE INVENTION

The presently disclosed subject matter overcomes some or all of the above-identified deficiencies of the prior art, as will become evident to those of ordinary skill in the art after a study of the information provided in this document.

Disclosed herein are biomimetic substrates with hierarchical architecture created by hot-pressing PCL into patterned laser-ablated nanopore molds. When extracted, these PCL substrates include polymer nanofibers patterned on the micron scale over square centimeters of culture substrate surface. The structures are similar in size and morphology to collagen fibrils universally found within mammalian cells [20, 24, 27]. The attachment of fibers at the substrate base mimics the basement membrane where collagen fibrils are in contact with a highly cross-linked collagen IV layer [28]. Altering the nanopore molds can control the spacing, length, diameter, and pattern of the polymer fiber matrix. Collectively, the molding methods described herein provide reproducible substrates that eliminate variability and precisely control fiber topography. When used to culture hMSCs, the polymer fiber models disclosed herein were found to significantly increase expression of critical regulators of self-renewal, as well as markers indicative of increased cell-cell interaction that are paramount in stem cell homeostasis [8-11].

Accordingly, in one aspect, the disclosure provides a cell culture substrate comprising: a polymer film and a patterned matrix of polymer nanofibers protruding from a surface of the polymer film, wherein the matrix is configured to modulate gene expression in cells cultured on or recruited to the matrix.

In another aspect, the disclosure provides an apparatus for studying stemness and cell-cell interactions in an in vitro environment, comprising: a polymer film and an array of polymer nanofibers protruding from a surface of the film, wherein the nanofiber array is arranged as a biomimetic matrix to mimic the extracellular matrix and basement membrane of a mammalian cell.

In yet another aspect, the disclosure provides a method of preparing a patterned nanofiber matrix, comprising: providing a mold having a patterned array of nanopores laser ablated in a surface thereof; pressing a thermoplastic polymer film against the mold surface; heating the polymer film to a temperature greater than the melting temperature the polymer film; allowing the polymer film to melt and infiltrate the nanopores; cooling the melted polymer to a temperature below the melting temperature of the polymer until the melted polymer solidifies; and removing the polymer from the mold as a patterned nanofiber matrix.

In still yet another aspect, the disclosure provides a method of preparing a patterned nanofiber matrix, comprising: providing a mold having a patterned array of nanopores laser ablated in a surface thereof; pressing a thermoplastic polymer film against the mold surface; heating the polymer film to a temperature greater than the glass transition temperature the polymer film such that the polymer film can flow and infiltrate the nanopores; cooling the polymer to a temperature below the glass transition temperature of the polymer until the polymer is sufficiently viscous to be removed from the mold; and removing the polymer from the mold as a patterned nanofiber matrix.

Numerous other objects, advantages and features of the present disclosure will be readily apparent to those of skill in the art upon a review of the following drawings and description of a preferred embodiment.

BRIEF DESCRIPTION OF THE SEVERAL VIEWS OF THE DRAWINGS

FIG. 1B is an enlarged view of the inset of FIG. 1A showing the position of the thermoplastic polymer film between the fused silica mold and a polycarbonate backing. The mold is backed by a fused silica blank.

FIG. 3A is a polymer fiber substrate overview showing the cut surface for transverse sections. FIG. 3B shows a 2×2 polymer fiber substrate. FIG. 3C shows a 2×3 polymer fiber substrate. FIG. 3D shows a 4×4 polymer fiber substrate. FIG. 3E shows a 5×5 polymer fiber substrate. FIG. 3F shows a 7×7 polymer fiber substrate. Scale bars are 10 μm.

FIG. 4A is a SEM of hMSCs on flat PCL. Scale bar is 37.5 μm. FIG. 4B is a SEM of hMSCs on 10×10 polymer fibers. Scale bar is 20 μm. FIG. 4C is an optical of hMSCs on flat PCL. Scale bar is 100 μm. FIG. 4D is an optical of hMSCs on 2×2 polymer fibers. Scale bar is 100 μm. FIG. 4E is an optical of hMSCs on 2×3 polymer fibers. Scale bar is 100 μm. FIG. 4F is an optical of hMSCs on 10×10 polymer fibers. Scale bar is 100 μm.

FIG. 5A shows Nanog expression relative to GAPDH. † Indicates $p<0.05$ relative to TCPS. ‡ Indicates $p<0.05$ relative to PCL spin coat. FIG. 5B shows OCT4a expression relative to GAPDH. † Indicates $p<0.05$ relative to TCPS. FIG. 5C shows PECAM expression relative to GAPDH. † Indicates $p<0.05$ relative to 4×4. ‡ Indicates $p<0.05$ relative to all other groups. FIG. 5D shows ITGA2 expression relative to GAPDH. † Indicates $p<0.05$ relative to all other groups.

DETAILED DESCRIPTION OF THE INVENTION

Figures 1A, 1B:
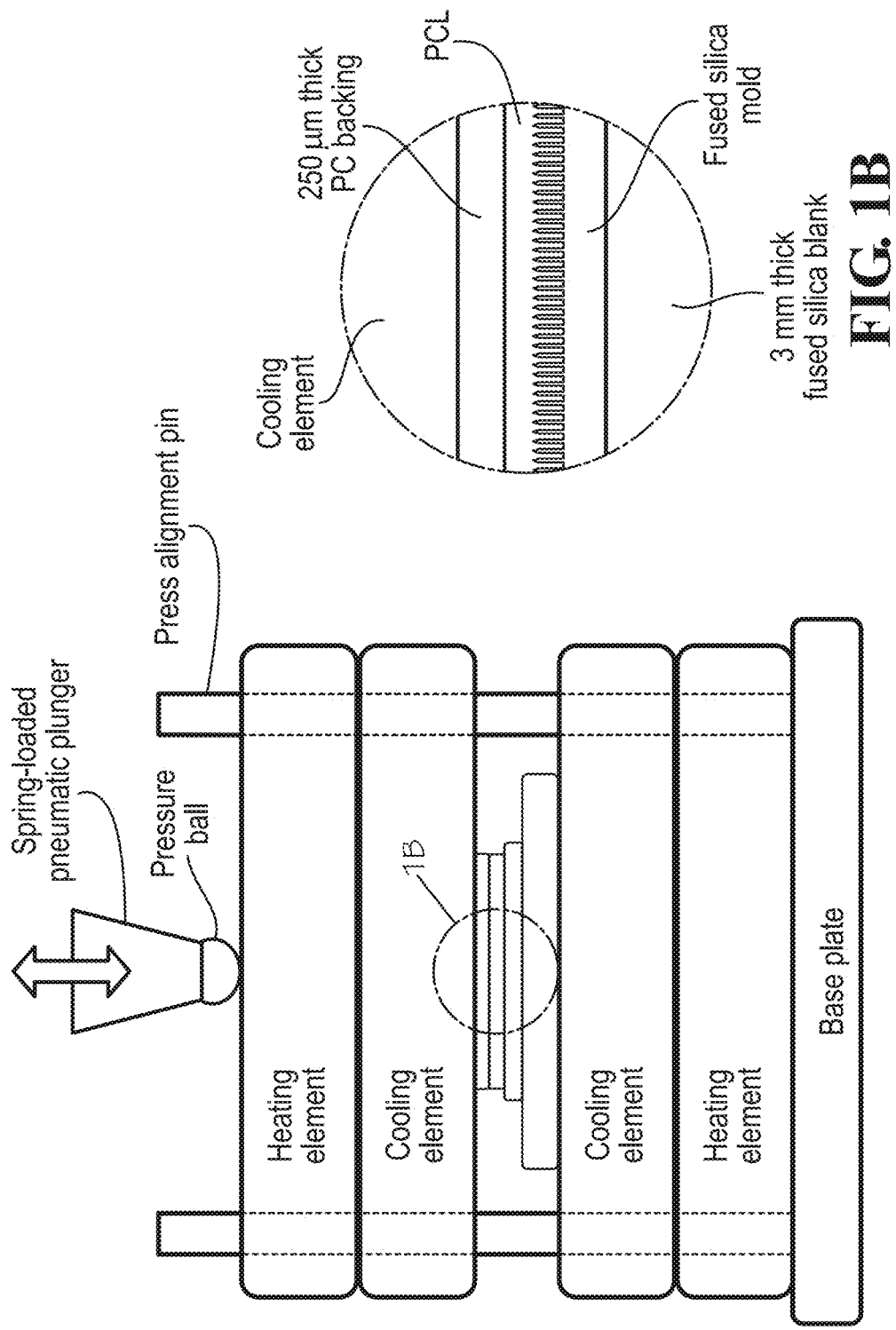
FIGS. 1A-B depicts the basic components and layout of an embodiment of a hot-pressing system.

The details of one or more embodiments of the presently disclosed subject matter are set forth in this document. Modifications to embodiments described in this document, and other embodiments, will be evident to those of ordinary skill in the art after a study of the information provided herein. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by one of ordinary skill in the art, definitions are set forth herein to facilitate explanation of the subject matter disclosed herein.

Unless defined otherwise, all technical and scientific terms used herein have the same meaning as commonly understood by one of ordinary skill in the art to which the subject matter disclosed herein belongs. Although any methods, devices, and materials similar or equivalent to those described herein can be used in the practice or testing of the presently disclosed subject matter, representative methods, devices, and materials are now described.

The terms "a", "an", and "the" refer to "one or more" when used in this application, including the claims. Thus, for example, reference to "a cell" includes a plurality of such cells, and so forth. The use of the word "a" or "an" when used in conjunction with the term "comprising" in the claims and/or the specification may mean "one," but it is also consistent with the meaning of "one or more," "at least one," and "one or more than one."

All references to singular characteristics or limitations of the present disclosure shall include the corresponding plural characteristic(s) or limitation(s) and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and devices of the present disclosure, including components thereof, can comprise, consist of, or consist essentially of the essential elements and limitations of the embodiments described herein, as well as any additional or optional components or limitations described herein or otherwise useful.

Unless otherwise indicated, all numbers expressing physical dimensions, quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently disclosed subject matter.

As used herein, the term "about," when referring to a value or to an amount of mass, weight, time, volume, concentration, percentage or a physical dimension such as length, width, or diameter, is meant to encompass variations of in some embodiments ±20%, in some embodiments ±10%, in some embodiments ±5%, in some embodiments ±1%, in some embodiments ±0.5%, and in some embodiments ±0.1% from the specified value or amount, as such variations are appropriate to perform the disclosed methods.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The present disclosure relates to the inventors demonstration that the patterned matrices of polymer nanofibers disclosed herein promote stemness and cell-cell interaction of stem cells in culture at least as efficiently as conventionally used cell culture substrates. Accordingly, in some embodiments, the disclosure is directed to a novel cell culture substrate. Embodiments of a cell culture substrate can include a polymer film and a patterned matrix of polymer nanofibers protruding from a surface thereof.

The polymer film can be any thermoplastic polymer. Examples of suitable thermoplastic polymers include poly (ε-caprolactone) (PCL), polyethylene oxide (PEG), polyvinyl chloride (PVC), polyvinyl formal (PVF), polyisoprene, trans (PI), polypropylene (PP), low-density polyethylene (LDPE), high-density polyethylene (HDPE), PIP castline (PiPc), PIP natural (PiPn), and polyvinylidene fluoride (PVDF). It should be understood that a blend of two or more such polymers can also be used.

By the term "patterned" it is generally meant that the polymer nanofibers disclosed herein are arranged or ordered into a user-defined pattern or array. In some embodiments, the term "patterned" can refer to the spacing of polymer nanofibers on a substrate. On a substantially flat substrate, such as a polymer film, the nanofibers disclosed herein can be spaced along an X-axis and a Y-axis at the same or different intervals along either axis. In some embodiments, nanofibers can be spaced about 50 µm, 40 µm, 30 µm, 20 µm, 10 µm, 9 µm, 8 µm, 7 µm, 6 µm, 5 µm, 4 µm, 3 µm, 2 µm, or 1 µm apart on an X-axis and about 50 µm, 40 µm, 30 µm, 20 µm, 10 µm, 9 µm, 8 µm, 7 µm, 6 µm, 5 µm, 4 µm, 3 µm, 2 µm, or 1 µm apart on a Y-axis. In an exemplary embodiment, the nanofibers are spaced about 2 µm apart along one axis, and about 3 µm apart along the other axis.

The term "matrix" as used herein refers generally to a structure or environment in which living cells can be cultured and "patterned matrix" refers to a matrix with engineered order. For example, a patterned matrix of polymer nanofibers can include a plurality of standing polymer nanofibers with user-defined physical dimensions arranged according to user-defined spatial parameters. User-tunable parameters include fiber spacing, diameter (also sometimes referred to herein as "width"), height (also sometimes referred to herein as "length"), and number of fibers per unit of surface area (also referred to herein as "fiber surface area density").

In some embodiments, a patterned matrix of polymer nanofibers can include nanofibers having an average length of at least 10.00 µm. In certain embodiments, the nanofibers can have a length of from about 10.00 µm to about 60.00 µm. In an exemplar embodiment, the nanofibers can have an average length of from about 15.00 µm to about 35.00 µm. In specific embodiments, the nanofibers can have a length of about 10.00 µm, 11.00 µm, 12.00 µm, 13.00 µm, 14.00 µm, 15.00 µm, 16.00 µm, 17.00 µm, 18.00 µm, 19.00 µm, 20.00 µm, 21.00 µm, 22.00 µm, 23.00 µm, 24.00 µm, 25.00 µm, 26.00 µm, 27.00 µm, 28.00 µm, 29.00 µm, 30.00 µm, 31.00 µm, 32.00 µm, 33.00 µm, 34.00 µm, 35.00 µm, 36.00 µm, 37.00 µm, 38.00 µm, 39.00 µm, 40.00 µm, 41.00 µm, 42.00 µm, 43.00 µm, 44.00 µm, 45.00 µm, 46.00 µm, 47.00 µm, 48.00 µm, 49.00 µm, 50.00 µm, 51.00 µm, 52.00 µm, 53.00 µm, 54.00 µm, 55.00 µm, 56.00 µm, 57.00 µm, 58.00 µm, 59.00 µm, or 60.00 µm.

In some embodiments, a patterned matrix of polymer nanofibers can include nanofibers having an average diameter of from about 0.10 µm to about 1.20 µm. In an exemplar embodiment, the nanofibers can have an average diameter of 0.24 µm to 0.34 µm. In certain embodiments, the nanofibers can have an average diameter of about 0.10 µm, 0.15 µm, 0.20 µm, 0.25 µm, 0.26 µm, 0.27 µm, 0.28 µm, 0.29 µm, 0.30 µm, 0.31 µm, 0.32 µm, 0.33 µm, 0.34 µm, 0.35 µm, 0.40 µm, 0.45 µm, 0.50 µm, 0.55 µm, 0.60 µm, 0.65 µm, 0.70 µm, 0.75 µm, 0.80 µm, 0.85 µm, 0.90 µm, 0.95 µm, 1.00 µm, 1.05 µm, 1.10 µm, 1.15 µm, or 1.20 µm.

The nanofiber substrate surface area density can range from about 1 to about 30 nanofibers per 100 µm$^2$. In some embodiments, the nanofiber surface area density can range from about 6 to about 25 nanofibers per 100 µm$^2$. In specific embodiments, the nanofiber surface density is about 6, 7, 8, 9, 10, 11, 12, 13, 14, 15, 16, 17, 18, 19, 20, 21, 22, 23, 24, or 25 nanofibers per 100 µm$^2$. In an exemplar embodiment, the nanofiber surface area density is about 16.7 nanofibers per 100 µm$^2$.

In certain embodiments, a matrix of polymer nanofibers is configured to modulate gene expression in stem cells cultured on or recruited to the matrix relative to control cells cultured in the absence of the matrix. As used herein, "modulate gene expression" refers to increasing or decreasing the expression of one or more genes encoding a polypeptide involved in cell self-renewal or cell-cell interaction, alone or in combination with other transcription and/or translational regulatory factors or nucleic acids encoding such a polypeptide. As used herein, the term "stem cell" can be any type of undifferentiated cell of a multicellular organism that is capable of giving rise to more cells of the same type, and from which certain other kinds of cell arise by differentiation. Stem cells can be either embryonic or adult stem cells. In an exemplar embodiment, the stem cells are human mesenchymal stem cells. The terms "culture" and "cultured" as used herein refer to the cultivation or maintenance of cells under conditions suitable for growth. The term "control cells" refers to cells of the same type cultured under the same conditions as cells cultured on the matrix, except that the control cells are cultured on TCPS or flat PCL in the absence of the matrix.

In specific embodiments, the patterned nanofiber matrix is configured to increase expression in cells cultured on or recruited to the matrix of a nucleic acid encoding a self-renewal transcription factor polypeptide or a cell-cell interaction marker polypeptide relative to control cells cultured in the absence of the matrix.

The terms "polypeptide" refers to a polymer of amino acids, or amino acid analogs, regardless of its size or function. Exemplary polypeptides include gene products, naturally occurring proteins, homologs, orthologs, paralogs, fragments and other equivalents, variants, and analogs of the foregoing.

The term "self-renewal transcription factor polypeptide" refers to any transcription factor that regulates transcription of genes involved in stem cell self-renewal. Exemplar self-renewal transcription factor polypeptides include homeobox protein Nanog (NANOG) and octomer-binding transcription factor 4A (OCT4A). In some specific embodiments, a self-renewal transcription factor polypeptide can be a polypeptide encoded by a nucleic acid that can be amplified by quantitative real-time PCR using the forward primer of SEQ ID NO: 1 and the reverse primer of SEQ ID NO: 2, or the forward primer of SEQ ID NO: 3 and the reverse primer of SEQ ID NO: 4.

The term "cell-cell interaction marker polypeptide" as used herein refers to any marker polypeptide that is indicative of cell-cell interaction. Exemplar cell-cell interaction marker polypeptide include platelet endothelial cell adhesion molecule 1 (PECAM) and integrin-α2 (ITGA2). In some specific embodiments, the cell-cell interaction marker polypeptide is a polypeptide encoded by a nucleic acid that can be amplified by quantitative real-time PCR using the forward primer of SEQ ID NO: 5 and the reverse primer of SEQ ID NO: 6, or the forward primer of SEQ ID NO: 7 and the reverse primer of SEQ ID NO: 8.

In another aspect, the present disclosure provides an apparatus for studying stemness and cell-cell interactions in an in vitro environment. The apparatus can comprise a polymer film and an array of polymer nanofibers arranged as a biomimetic matrix protruding from a surface of the film. The term "biomimetic," as used in connection with a matrix disclosed herein, refers to a matrix that is configured to mimic the function and/or structure of the extracellular matrix and basement membrane of a mammalian cell.

The presently disclosed subject matter further relates to a method of fabricating a patterned nanofiber matrix. The method includes the steps of providing a mold having a patterned array of nanopores laser ablated in a surface thereof and pressing a thermoplastic polymer against the mold surface. Non-limiting examples of suitable thermoplastic polymers include poly(ε-caprolactone) (PCL), polyethylene oxide (PEG), polyvinyl chloride (PVC), polyvinyl formal (PVF), polyisoprene, trans (PI), polypropylene (PP), low-density polyethylene (LDPE), high-density polyethylene (HDPE), PIP castline (PiPc), PIP natural (PiPn), and polyvinylidene fluoride (PVDF). It should be understood that a blend of two or more such polymers can also be used. In an exemplar embodiment, the thermoplastic polymer is in the form of a film.

In an exemplar embodiment, the polymer is pressed against the nanopore mold using a force of about 50 PSI. However, in other embodiments, the polymer can be pressed against the nanopore mold under 0 PSI to about 100 PSI of pressure. One of skill in the art will recognize that the amount of force used to press the polymer against the nanopore mold can vary depending on the temperature of the polymer during the pressing step.

The method can further include the steps of heating the polymer film to a first temperature, and holding the polymer film at the first temperature for a period of time sufficient to allow the polymer to infiltrate the nanopores. In one embodiment, the first temperature in a temperature equal to or greater than the melting temperature of the polymer. In another embodiment, the first temperature is a temperature equal to or greater than the glass transition temperature of the polymer. In some embodiments, holding the polymer film at the first temperature for a period of time sufficient to allow the polymer to infiltrate the nanopores comprises allowing the polymer film to melt. In some embodiments, holding the polymer film at the first temperature for a period of time sufficient to allow the polymer to infiltrate the nanopores comprises holding the polymer film at the first temperature for a period of time sufficient to lower the viscosity of the polymer film such that the polymer can flow into the nanopores.

The applicable glass transition and melting temperatures can vary between polymers, as can the length of time at which the temperature is held at or above the glass transition or melting temperature of the polymer to allow the film to flow or melt and infiltrate the nanopores of the mold. In some embodiments, the first temperature can range from about 65° C. to about 220° C. In some embodiments, the first temperature can be from about 80° C. to 180° C. In one embodiment, the first temperature is about 150° C. and the hold time is about 5 minutes.

The method further comprises the steps of cooling the polymer to a second temperature wherein the second temperature is less than the first temperature, and removing the solidified polymer from the mold as a patterned nanofiber matrix. In some embodiments, the second temperature is a temperature equal to or less than the melting temperature of the polymer. In additional embodiments, the second temperature is a temperature equal to or less than the glass transition temperature of the polymer. In some embodiments, cooling the polymer to a second temperature comprises cooling melted polymer to a temperature below the melting temperature of the polymer until the melted polymer solidifies. In such embodiments, the solidified polymer can then be removed from the mold as a patterned nanofiber matrix. In additional embodiments, cooling the polymer to a second temperature comprises cooling the polymer to a temperature below the glass transition temperature of the polymer until the polymer becomes sufficiently viscous to be removed from the mold while maintaining the structural integrity of the viscous polymer.

In some embodiments, cooling the polymer comprises allowing the polymer to cool by air convection to room temperature. In other embodiments, cooling the polymer comprises allowing the polymer to cool by air convection to a temperature of about 50° C., then rapidly cooling the polymer to room temperature. In some embodiments, rapid cooling of the polymer to room temperature is achieved by circulating cold water through a portion of a press in which the polymer is seated, such as a cooling element. In still other embodiments, cooling the polymer can comprise actively cooling the polymer to room temperature using cooling methods known in the art. In one exemplar embodiment, cooling the polymer comprises cooling the melted polymer to a temperature below the melting temperature of the polymer until the melted polymer solidifies.

The presently disclosed subject matter is further illustrated by the following specific but non-limiting examples. The following examples may include compilations of data that are representative of data gathered at various times during the course of development and experimentation related to the present invention.

Example 1

This example employed novel cell culture substrates created by hot-pressing poly(ε-caprolactone) films in femtosecond laser-ablated nanopore molds to form patterned polymer nanofiber matrices on flat PCL substrates. Quantitative real-time polymerase chain reaction and immunocytochemistry were used to show that these polymer nanofiber matrices increased expression of several critical self-renewal factors and markers of cell-cell interaction, thereby maintaining stemness of hMSCs cultured thereon.

Materials and Methods

All reagents were purchased from Sigma-Aldrich (St. Louis, Mo.) at the highest available quality unless otherwise noted.

Culture Substrate Fabrication

For this work, a one millimeter thick, double side polished fused silica wafer (Mark Optics, Santa Ana, Calif.) was diced into 22 mm by 22 mm square chips. Each chip was patterned with a single 10 mm by 10 mm array of nanopores using the femtosecond laser machining system [29]. Each array was patterned with a unique pore-to-pore spacing value, determined by the choice of laser beam raster, laser pulse repetition rate and laser beam scanning rate. Each nanopore was formed by a single 790 nm wavelength, 160 femtosecond laser pulse focused on the surface of the fused silica chip using a dry microscope objective (Nikon CF Plan Achromat 79173) with a numerical aperture (NA) of 0.85 and spherical aberration correction collar set to 0.17 mm. The as-processed fused silica molds were soaked in aqueous KOH at 90° C. to remove femtosecond laser ablation debris and also to enlarge the diameter of the nanopores. The etched molds were rinsed then soaked in deionized water at 90° C. for 2 h to remove residual KOH, and finally dried under a stream of dry nitrogen.

To facilitate the release of polymer fibers from the mold, all fused silica molds were silanized with 1H1H2H2H Perfluorodecyltrichlorosilane (FDTS) (Alfa Aesar, Ward Hill, Mass.). First the molds were conditioned in a 1:1 mix of HCl:methanol for 30 min. The molds were then rinsed in methanol, dried under a stream of dry nitrogen, and finally exposed to FDTS vapors inside a 200 millitorr desiccator for 12 h. FTDS molecules bind to —OH terminated surfaces and form self-assembled monolayers that reduce surface energy and prevent sticking.

Each mold listed in Table 1 was used to prepare PCL nanofiber culture models via hot-pressing. A piece of PCL film, formed by compression of PCL pellets, was placed between a fused silica mold and a 22 mm by 22 mm by 0.25 mm HybriSlip HS22-CS polycarbonate ("PC") backing slide (Grace Bio-labs, Bend, Oreg.). This three-element stack was prepared atop a 3 mm thick fused silica flat blank seated at the center of the press (FIGS. 1A-B) With all the elements of the press stacked together, the spring-loaded pneumatic plunger was actuated progressively to a pressure of 45 psi, pressing the pressure ball against the stack. The Chrome-Nickel heating elements inside the heating blocks were turned on, and the temperature of the cooling elements (monitored using a pair of thermocouples) was raised to and held at 80° C. for 5 min. During this period, the PCL melted and infiltrated the nanopores of the mold. The heating elements were then turned off, and the press allowed to cool to 50° C. by air convection. Once the temperature of the cooling elements reached 50° C., rapid cooling to room temperature was forced by circulating cold water through the cooling elements. Once room temperature was reached, the plunger was allowed to pull back to its the position. The mold-PCL-PC stack was removed from the press, and PCL-PC was gently peeled-off the mold. The PCL adhered strongly to the PC backing, making it easy to handle.

Flat PCL substrates were formed by the press apparatus, and spin-coated control-substrates were formed by a spin-coating apparatus (Laurell Technologies, North Wales, Pa., USA). For spin-coated substrates 15 mm circular glass cover slips (Fisher Scientific) were first cleaned with 100% ethanol, rinsed with deionized water, and heated to 80° C. for ~20 min to dry. A 1% \A/eight/volume (w/v) solution of PCL in tetrahydrofuran (THF) was spun for 30 s at 3000 RPM atop the clean glass cover slip (50 µl polymer solution/sample).

Substrate Characterization

For scanning electron microscopy ("SEM") imaging of polymer fibers, we used JEOL JSM-6320 F (JEOL, Tokyo, Japan). Samples for SEM imaging were prepared by cross sectioning PCL on PC substrates with a razor blade. To prevent PCL films from charging during SEM imaging, every sample was sputter-coated with a 20-30 nm thick gold film using a Bio-Rad Polaron SEM coating system E5150 with film thickness control (QuorpmTechnologies, UK). Polymer fiber dimensions were measured using ImageJ (NIH, Bethesda, Md.). During the mold fabrication process, the laser pulse created an entrance hole in the mold that had a larger diameter than the majority of the hole. This resulted in a wider base on each polymer fiber that was 1-2 µm in height. These bases were excluded from the fiber diameter measurement. Fifteen diameter measurements were performed on two images per each polymer fiber mold. These measurements include the sputter coating thickness. The height of fibers above the base was measured by optical microscopy. A 50× objective was focused, at first, on the substrate, and then translated vertically until the tops of the fibers were in focus. The translation distance was measured on a micrometer. Focus was verified using brightfield and darkfield functions. Optical height measurements are consistent with SEM imaging.

Cell Culture hMSCs were purchased from Lonza (Walkersville, Md.). All cell experiments used hMSCs at passage 5. hMSCs were cultured in alpha-minimum essential media with nucleosides (Life Technologies, Carlsbad, Calif.), 16.7% heat-inactivated fetal bovine serµm (Life Technologies), 1% penicillin/streptomycin (Life Technologies), and 4 µg/ml plasmocin prophylactic agent (InvivoGen, San Diego, Calif.). Cells were grown in a humidified incubator at 37° C. and 5% $CO_2$. Media was replaced every 3 days. Human MSCs were detached from tissue culture flasks at around 80% confluence with 0.05% trypsin-EDTA and passaged at 100-500 cells/$cm^2$. For all cell experiments, hMSCs were seeded on substrates at a density of 10,000 viable cells/$cm^2$. Cell media was replaced after 72 h.

Quantitative Real-Time Polymerase Chain Reaction (qPCR)

Cells cultured on polymer fiber films and TCPS control wells were homogenized with Trizol reagent (Life Technologies), mixed with chloroform (1:5 Trizol:chloroform), and separated by centrifugation (12,000×g, 15 min, 4° C.). The aqueous phase containing RNA was isolated using RNeasy columns (Bio-Rad, Hercules, Calif.) according to the manufacturer's instructions. RNA concentration was determined using a TECAN M1000 plate reader with the manufacturer's software. cDNA was synthesized using a cDNA generation kit (Applied Biosystems, Life Technologies, Carlsbad, Calif.) and qPCR was performed using SYBR Green master mix kit (Bio-Rad) with 15 ng cDNA and 500 mM each of forward and reverse primers. Primer sequences were the following: Nanog (NM_024865.2) forward SEQ ID NO: 1 and reverse SEQ ID NO: 2; OCT4A (NM_002701.4) forward SEQ ID NO: 3 and reverse SEQ ID NO: 4; ITGA2 (NM_002203.3) forward SEQ ID NO: 5 and reverse SEQ ID NO: 6; PECAM (NM_00442.4) forward SEQ ID NO: 7 and reverse SEQ ID NO: 8; and GAPDH (NM_002046.4) forward SEQ ID NO: 9 and reverse SEQ ID NO: 10. A CFX Real-Time PCR System (Bio-Rad) was run with the qPCR protocol: 95° C. for 3 min, followed by 40 cycles of denaturation at 95° C. for 30 s, annealing at 58° C. for 30 s, and extension at 72° C. for 30 s. Expression of each gene measured was normalized to the expression of glyceraldehyde 3-phosphate dehydrogenase ("GAPDH") as a housekeeping gene, thereby generating ΔC(t) values, and expression of $2^{-\Delta\Delta C(t)}$ relative to the TCPS control. N=3 biological replicates per substrate condition were performed.

Immunocytochemistry

Cells cultured on the test substrates were fixed with 4% paraformaldehyde ("PFA") for 15 min at room temperature and permeabilized with 10% goat serum with 0.3% Triton-X overnight at 4° C. Cells were then incubated with Hoechst (2 µg/ml) for 20 min at room temperature, followed by Alexa488-phallodin (1:5 v/v in PBS, Life Technologies, Carlsbad, Calif.) for 10 min. Imaging was performed with a Zeiss LSM 710 confocal microscope (Carl Zeiss, Oberkochen, Germany) and images were process with Zeiss Zen software and ImageJ (NIH, Bethesda, Md.).

Results and Discussion

Polymer Fiber Substrate Fabrication

Recently, Rajput and co-workers [29] demonstrated a novel and simple process of fabricating polymer films covered with large arrays of standing polymer fibers that mimic the fibrillar environment found in the extracellular matrix. In this process, a polymer-solvent solution is cast on the surface of a fused silica mold where an array of ultra-high aspect ratio surface nanopores is formed via the femtosecond laser ablation method first described by White et al. [30]. The polymer-solvent solution fills the surface nanopores through capillary action, and as the solvent dissipates, polymer fibers form within these nanopores. Once the solvent evaporates completely, the resulting polymer film is gently peeled-off the surface of the fused silica chip, producing an array of standing polymer fibers.

Here, nanofibers were fabricated using a new technique of hot-pressing, a solvent-free process applicable to thermoplastic polymers. In the hot-pressing method, the polymer film and the fused silica mold are pressed against each other and warmed above the polymer melting temperature for 5 minutes, allowing molten polymer to flow into the nanopores of the mold surface. Once the materials return to room temperature, the resulting nanofiber polymer film is peeled off the mold. This process is much faster than solvent casting and yields more fully formed fibers with fewer defects than the casting process. Hot pressing also eliminates the use of solvents which in trace amounts can affect cell fate. The omission of solvent eliminates the need to functionalize the polymer nanofibers with silica or other coatings before culturing stem cells directly on the fibers. A wider range of chemical dopants can also be used when polymer solvents are eliminated.

Ultra-high aspect ratio nanopore molds can be machined with any pattern of holes or lines with the femtosecond laser to generate the nanofiber arrays with complex geometries [31-34]. Table 1 lists the various layouts used here, and the basic components of a hot-pressing system are shown in FIG. 1A and FIG. 1B. As ablated, the nanopores have diameters as small as 50 nm at the bottom and entrance holes as small as 150 nm. The diameter and depth of the nanopores can be adjusted by varying the focus depth and laser energy per laser pulse. Nanopores can be etched in hot potassium hydroxide ("KOH") to further enlarge the diameters up to 1 µm. The hydroxide has high specificity (>100:1) for laser-damaged silica, which occurs in the diffraction-limited focal spot surrounding the nanopore. With these parameters of fabrication, the reusable fused silica molds can be prepared with over 25 million nanopores per square centimeter.

TABLE 1

Mold identification with process times and resulting polymer fiber measurement statistics

| Silica Mold ID | Pore spacing X axis (µm) | Pore spacing Y axis (µm) | Nanopores per area (100 µm$^2$) | Laser Energy per pulse (µJ) | KOH etch time, molarity (hours, Molarity) | Fiber width mean ± SEM (µm) | Fiber height mean ± SEM (µm) |
|---|---|---|---|---|---|---|---|
| 2 × 2 | 2 | 2 | 25 | 1.4 | 1, 10M | 0.15 ± 0.03 | 30.0 ± 5.0 |
| 2 × 3 | 2 | 3 | 16.7 | 2 | 1, 10M | 0.29 ± 0.05 | 25.0 ± 10.0 |
| 4 × 4 | 4 | 4 | 6.2 | 2 | 1, 10M | 0.27 ± 0.05 | 30.0 ± 5.0 |
| 5 × 5 | 5 | 5 | 4 | 4 | 3, 5M | 0.46 ± 0.05 | 30.0 ± 5.0 |
| 7 × 7 | 7 | 7 | 2 | 1.8 | 2, 10M | 1.10 ± 0.08 | 25.0 ± 0.5 |
| 8 × 8 | 8 | 8 | 1.5 | 1.8 | 2, 10M | 0.91 ± 0.07 | 16.0 ± 0.3 |
| 10 × 10 | 10 | 10 | 1 | 2 | 2, 10M | 0.92 ± 0.07 | 24.0 ± 1.0 |

Figure 2A:
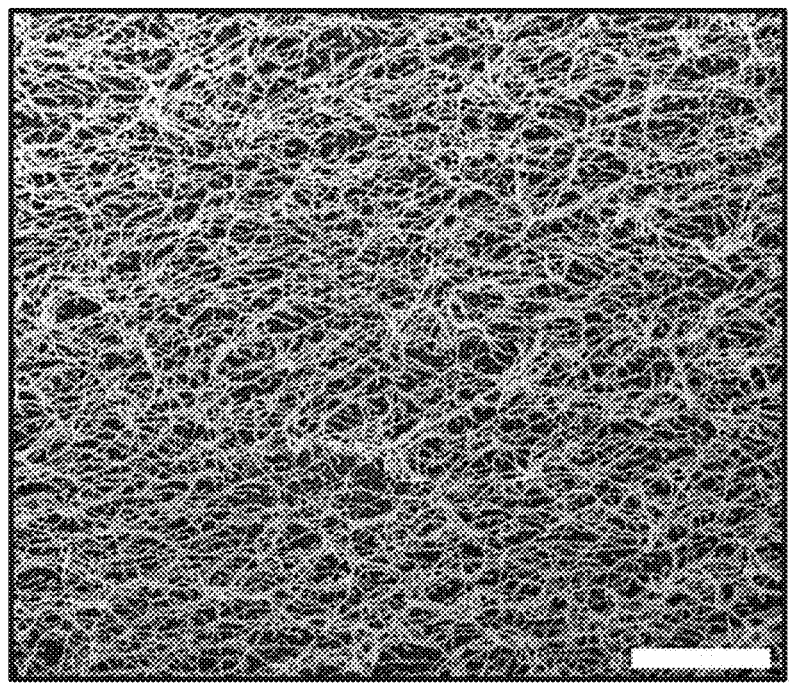
FIGS. 2A-B are scanning electron micrographs of two small fiber models taken parallel to the substrate at the same magnification. The 2×2 pattern shown in FIG. 2A has the smaller diameter fibers and the highest density of fibers at 25 per 100 μm$^2$. The 5×5 mold shown in FIG. 2B has larger diameter fibers and a density of 4 fibers per 100 μm$^2$. Scale bars are 20 μm.
Figure 2B:
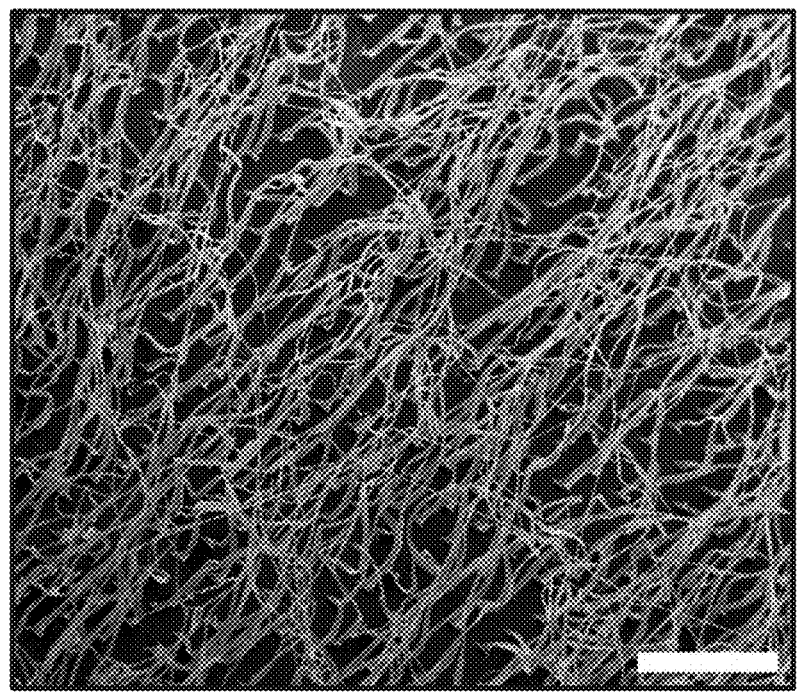
Figure 3A:
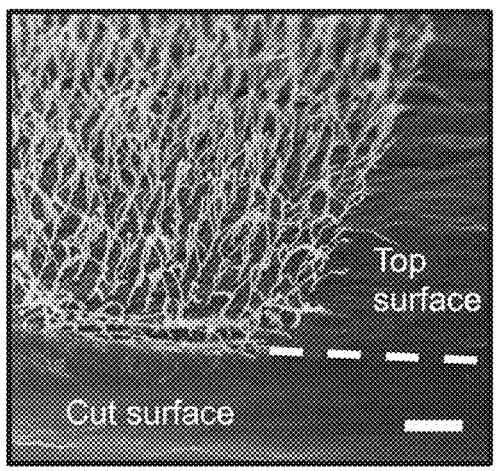
FIGS. 3A-F include transverse sections of freestanding polymer fiber films.
Figure 3B:
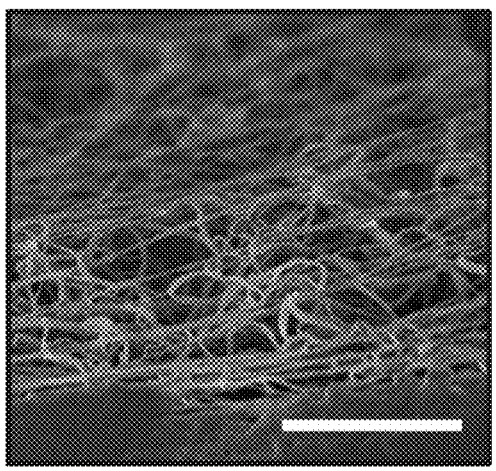
Figure 3C:
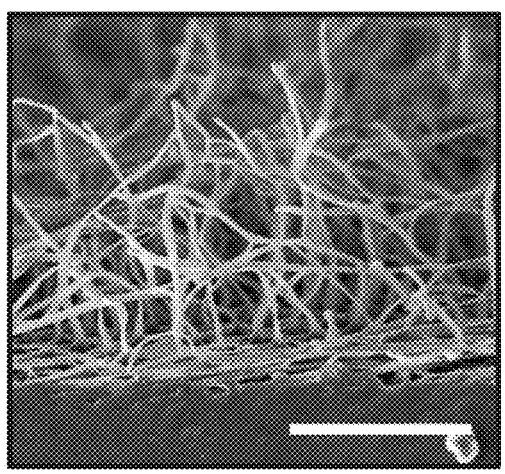
Figure 3D:
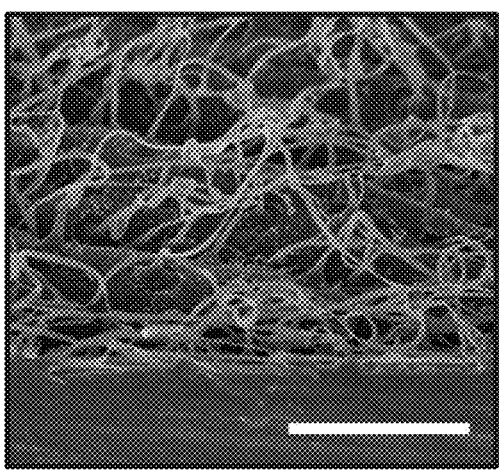
Figure 3E:
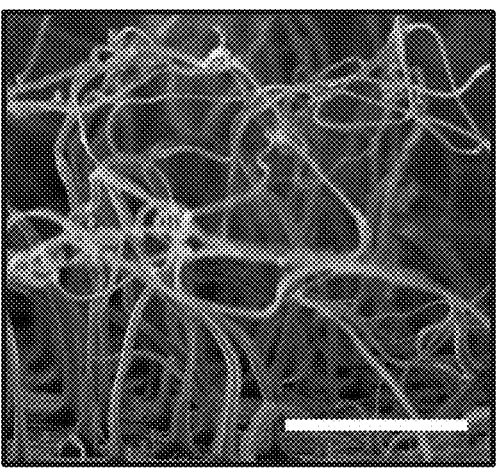
Figure 3F:
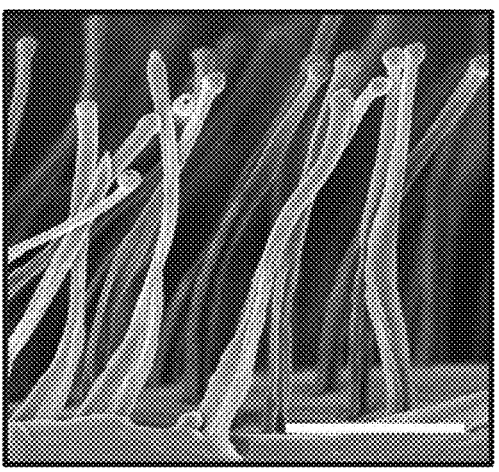

Long polymer fibers can be formed in and extracted from high aspect ratio nanopores via casting, previously mentioned, or hot-pressing as described here. SEM images of typical arrays of PCL polymer fibers formed by hot-pressing are shown in FIGS. 2A-B. Transverse sections of the fiber models are shown in FIGS. 3A-F. Average diameters and height of the fiber mat are given in Table 1. Polymer fiber morphology depends on etch time. In all conditions, fiber structures were observed to be wider at the base than at the tip, similar to the nanopore morphology reported previously [29]. Substrates formed using 2×2, 2×3, 4×4, and 5×5 molds had average fiber diameters under 500 nm and average fiber lengths greater than 30 µm. Substrates formed using 7×7, 8×8, and 10×10 molds yielded fibers with average diameters around 1 µm and lengths between 15 and 25 µm. Employing two-hour etch times resulted in larger pore size and larger fiber diameters. Polymer fibers in the 2×2, 2×3, 4×4, and 5×5 did exhibit some stretching of the polymer fibers during removal from the mold, but these deformations were not significant such that consistency in fabrication was compromised. Overall, these results demonstrate the tunability of fiber morphology using the hot-pressing technique.

hMSC Response to Polymer Fiber Models hMSCs were cultured on flat or polymer nanofiber substrates for 96 hours in order to allow for the cells to completely acclimate to their culture substrate, which includes recognizing the presence of the substrate, receiving the outside-in material cues, altering cell gene and protein expression, and implementing the new cell morphology/tissue structure. The substrates themselves did not degrade during the culture period and the polymer nanofibers could still be seen by brightfield microscopy. The integrity of the polymer substrates was also maintained during the media change and no media leakage was observed between the PCL and the polycarbonate backing.

Figure 4A:
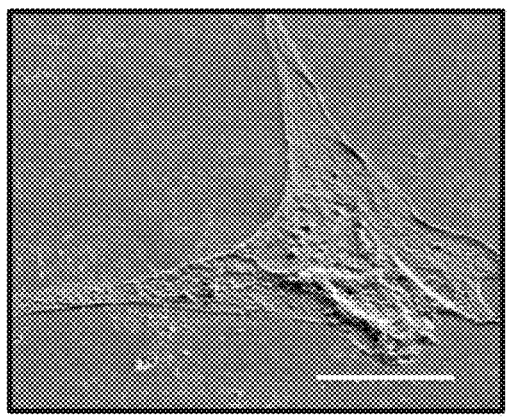
FIGS. 4A-F include optical and SEM images of hMSCs on various polymer culture models showing hMSC responses to such models.
Figure 4B:
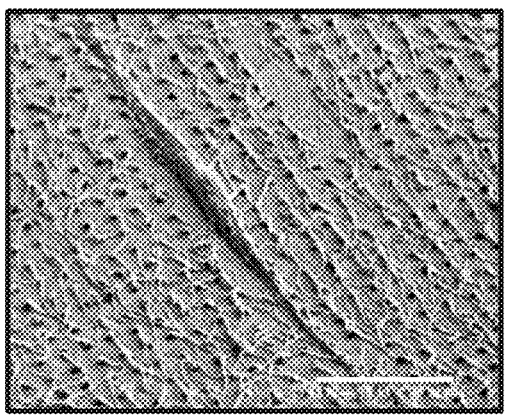
Figure 4C:
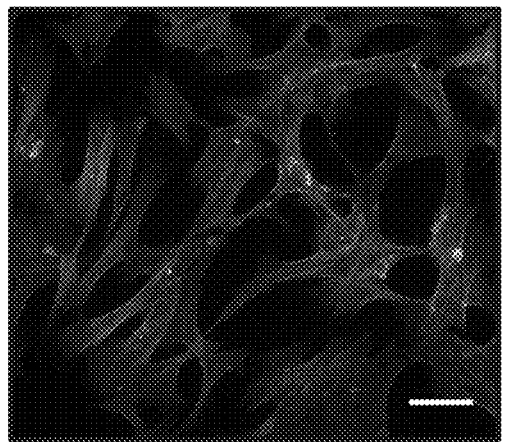
Figure 4D:
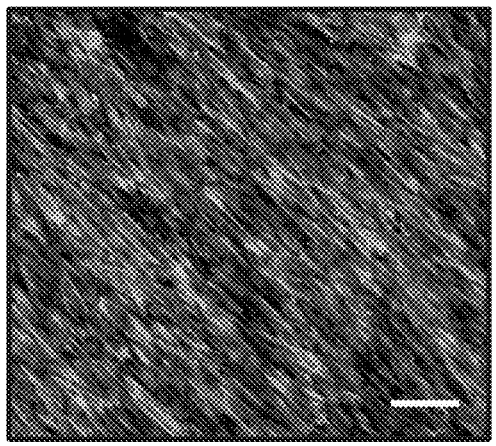
Figure 4E:
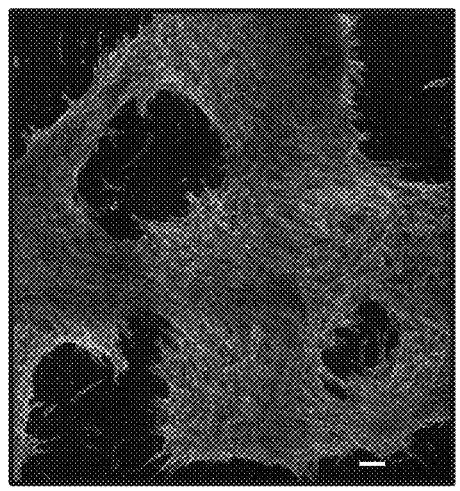
Figure 4F:
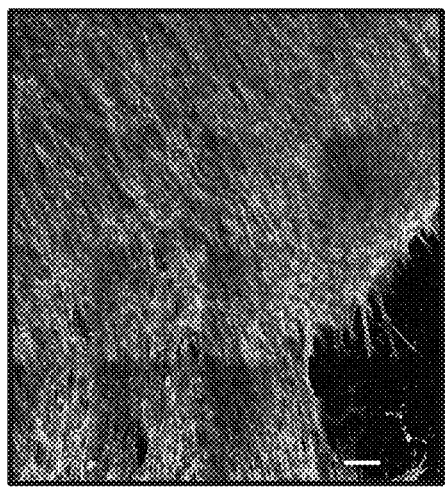

On the flat PCL substrates, prominent hMSC spreading morphology with large, wide membrane protrusions that maximized cell membrane surface contact area with the polymer was observed (FIGS. 4A and 4C). These cells also demonstrated non-specific organization of their actin cytoskeleton (FIG. 4C). When cultured on polymer nanofiber substrates, hMSCs were observed to interact directly with the polymer nanofibers (FIG. 4B) and were strictly oriented along rows of fibers with a more spindle shape morphology. This observation has been well documented with micro-patterned substrates in numerous other studies and is termed "contact-guidance" [35]. Only when cultured on polymer nanofibers were hMSCs seen to organize into tissue-like morphologies, complete with alignment of actin cytoskeleton (FIG. 4D). Interestingly, large-scale tissue-like structures were regularly observed on polymer nanofiber models regardless of spacing (FIGS. 4E and 4F).

Gene Expression Analysis

Figure 5A:
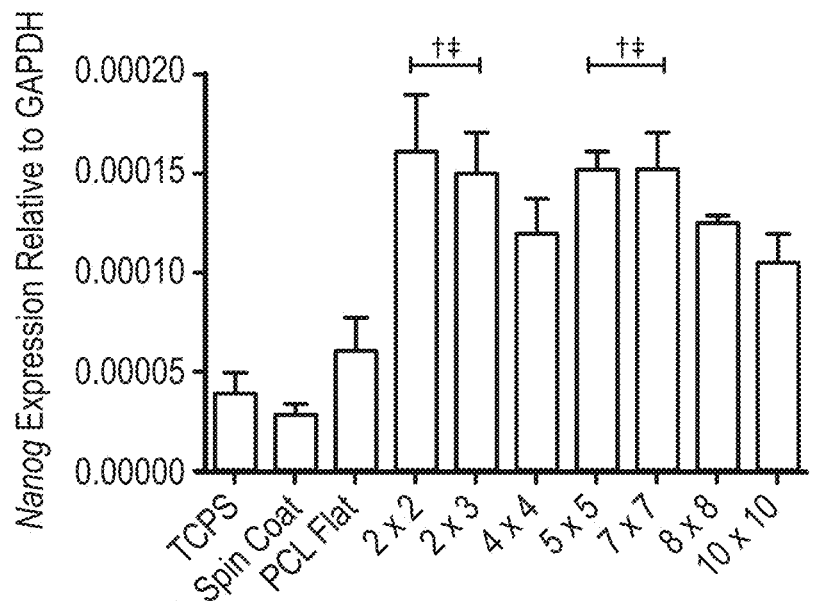
FIGS. 5A-D include a set of graphs that show expression of different genes by hMSCs on different polymer fiber substrates.
Figure 5B:
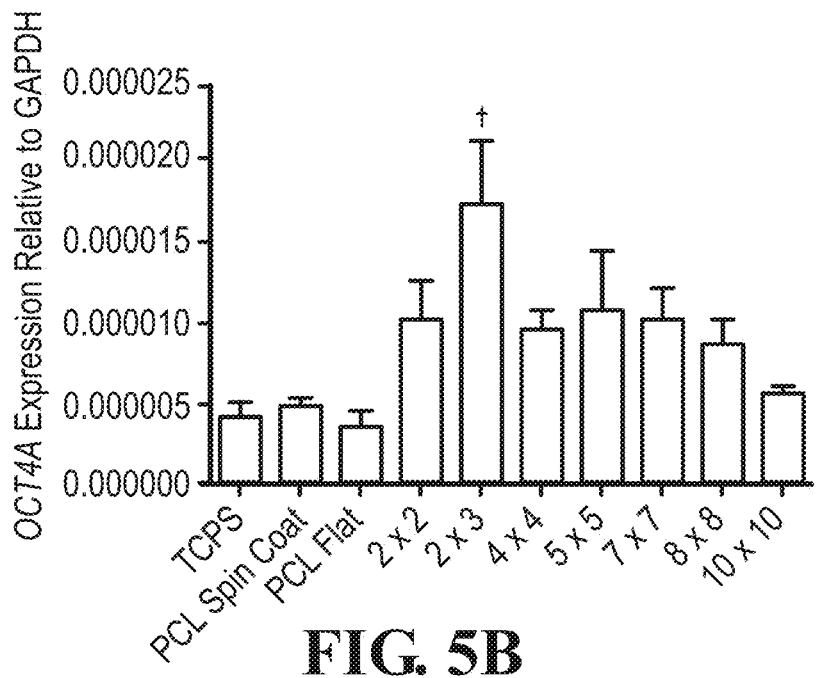
Figure 5C:
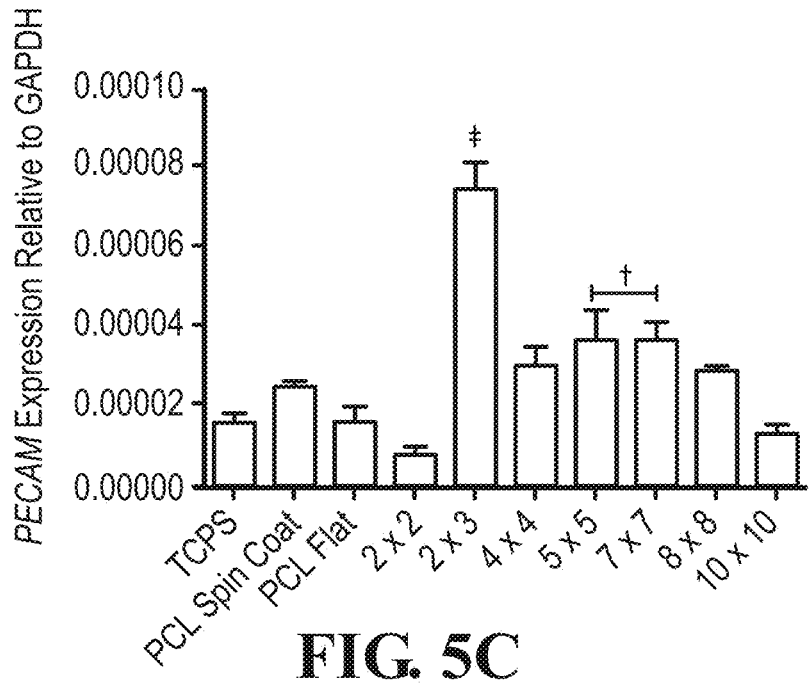
Figure 5D:
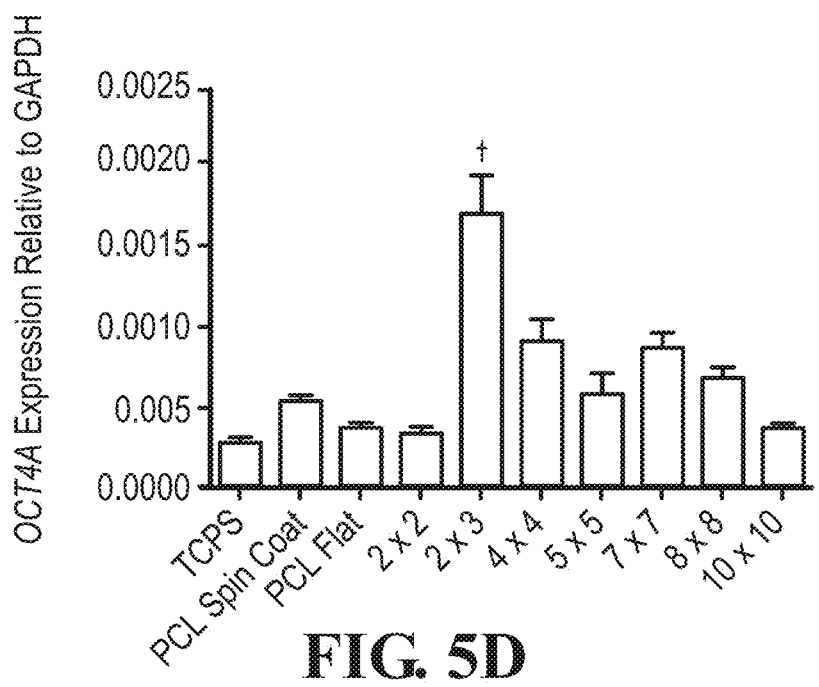

When cultured directly on polymer nanofiber substrates for 4 days, hMSCs unexpectedly and significantly increased expression of the transcription factors Nanog and OCT4A, which are critical for self-renewal of stem cells [36]. This increase in gene expression was most significant on 2×3 models, but remained increased over TCPS and flat PCL controls for all polymer fiber templates (FIGS. 5A and 5B). These findings also appear to positively correlate with the presence of tissue-like structures that formed only on the polymer nanofiber substrates. With respect to cell adhesion interactions, hMSCs exhibited significantly higher cell-cell interactions and lower cell-matrix interactions compared to cells on the flat substrates (FIGS. 5C and 5D). These results are visually supported by the morphologies of hMSCs cultured on polymer nanofiber and flat models (FIGS. 4A and 4C). The significant increase in expression of platelet endothelial cell adhesion molecule 1 ("PECAM"), an indicative marker of cell-cell interaction, peaked on the 2×3 model (FIG. 5C) [37, 38]. In addition, culture on polymer nanofiber substrates increased the expression of integrin subunit alpha 2 ("ITGA2"), which also is indicative of increased cell-cell interaction (FIG. 5D) [39].

Many studies investigating basic MSC physiology utilize "hanging drop" models as this culture platform has been reported as the best available bone marrow-analog culture model in a 3D format [40]. MSCs in this setting secrete their own matrix to allow for cell-matrix adhesion events, but the additional presence of cell-cell adhesion events given the substrate-less format of the hanging drop model appears to be mimicked by the polymer nanofiber substrates. As such, the 2×3 model likely provided the same balance of available cell-matrix adhesion by the surface area of the nanofibers themselves, covering any flat PCL underneath the fibers that would overcome potential cell-cell adhesion events known to occur among hMSCs. In conclusion, these results indicate that varying polymer fiber spacing can alter cell-cell and cell-matrix interactions.

Example 2

This example employed the novel hot-pressing method to identify additional thermoplastic polymers suitable for use in the fabrication of patterned polymer nanofiber matrices from laser ablated nanopore molds.

Fabrication of Polymer Fiber Substrates from Additional Polymers

Figure 6:
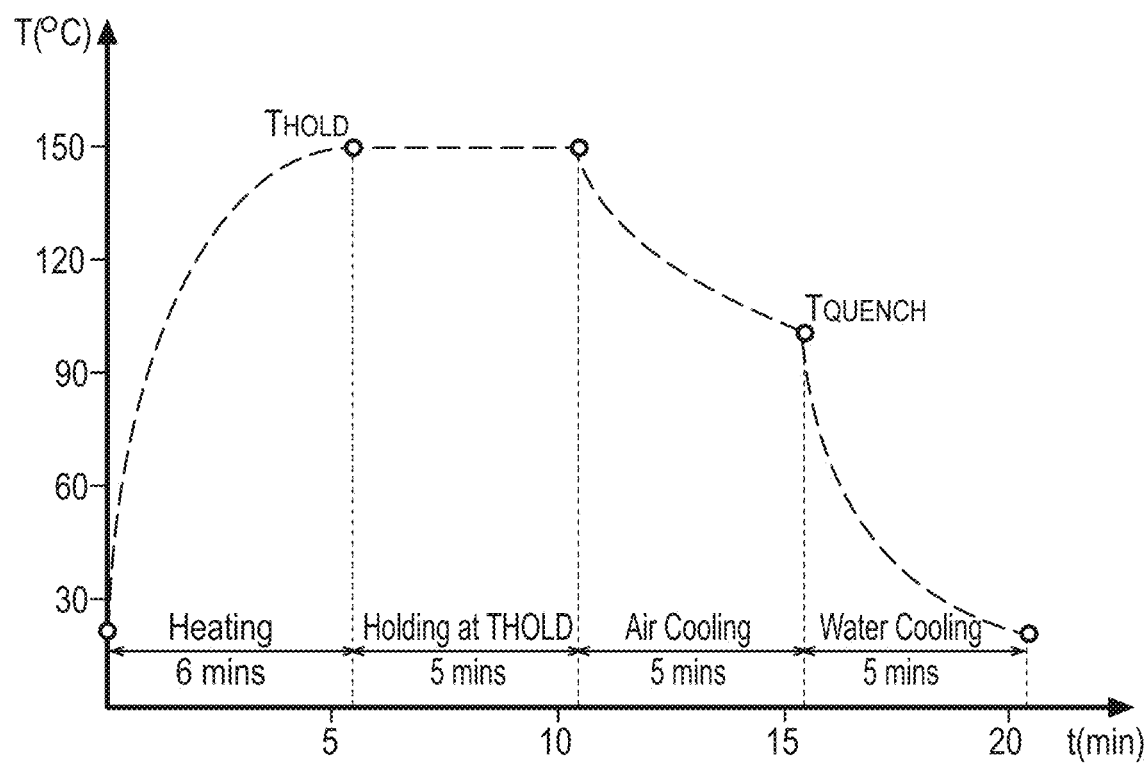
FIG. 6 is a graph showing one embodiment of a thermal cycle profile for hot-embossing a thermoplastic polymer having a melting temperature of 150° C. or less.
Figure 7:
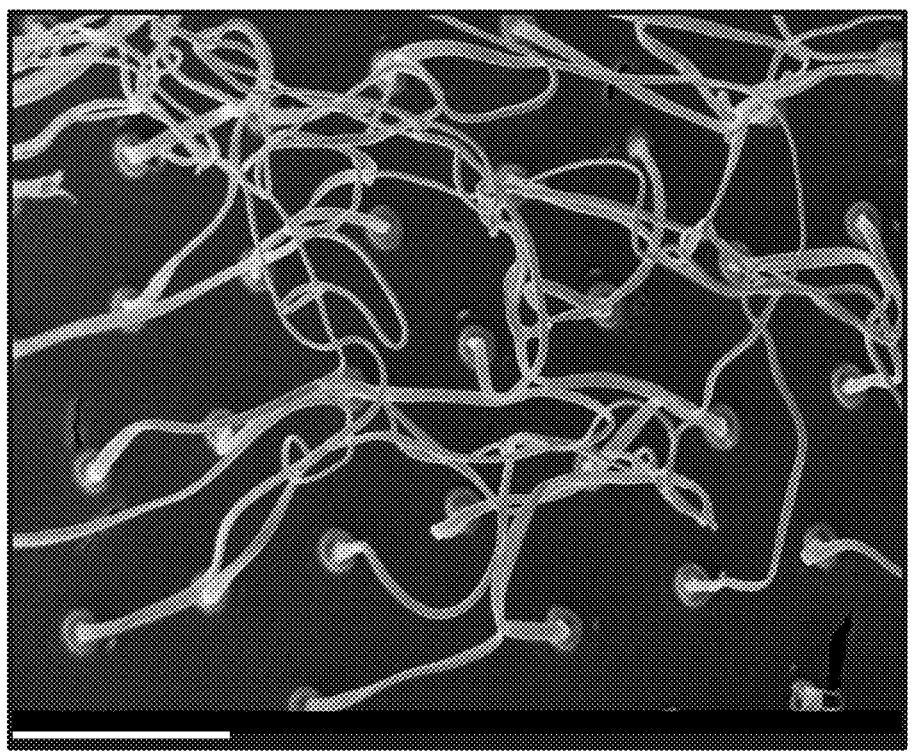
FIG. 7 is a SEM image of PCL nanofibers hot-embossed from a patterned laser-ablated nanopore mold. Scale bar is 10 μm.
Figure 8:
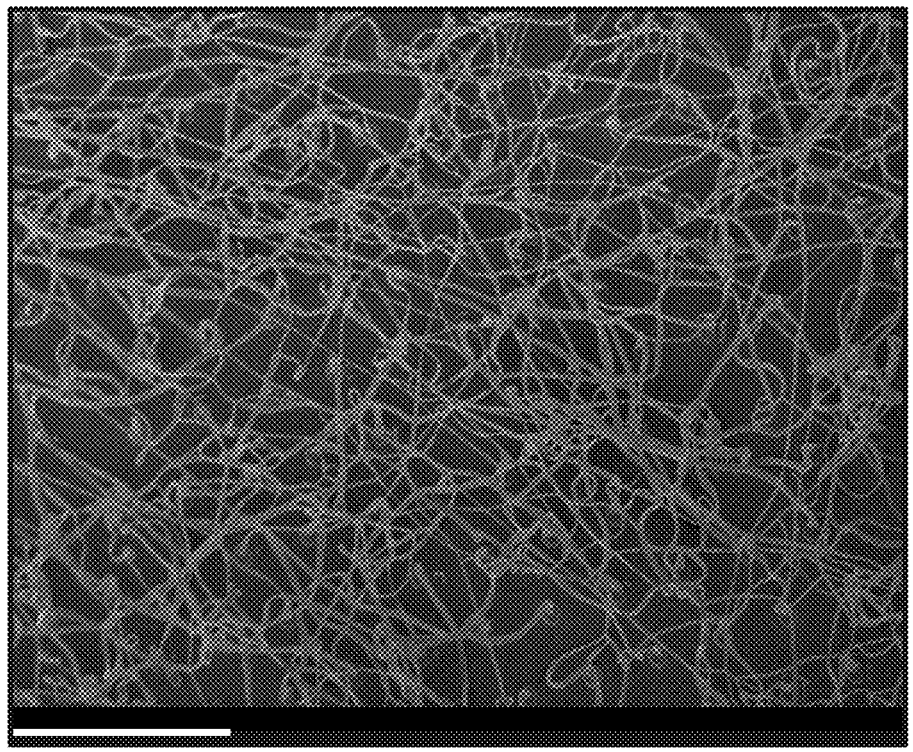
FIG. 8 is a SEM image of PEG nanofibers hot-embossed from a patterned laser-ablated nanopore mold. Scale bar is 20 μm.
Figure 9:
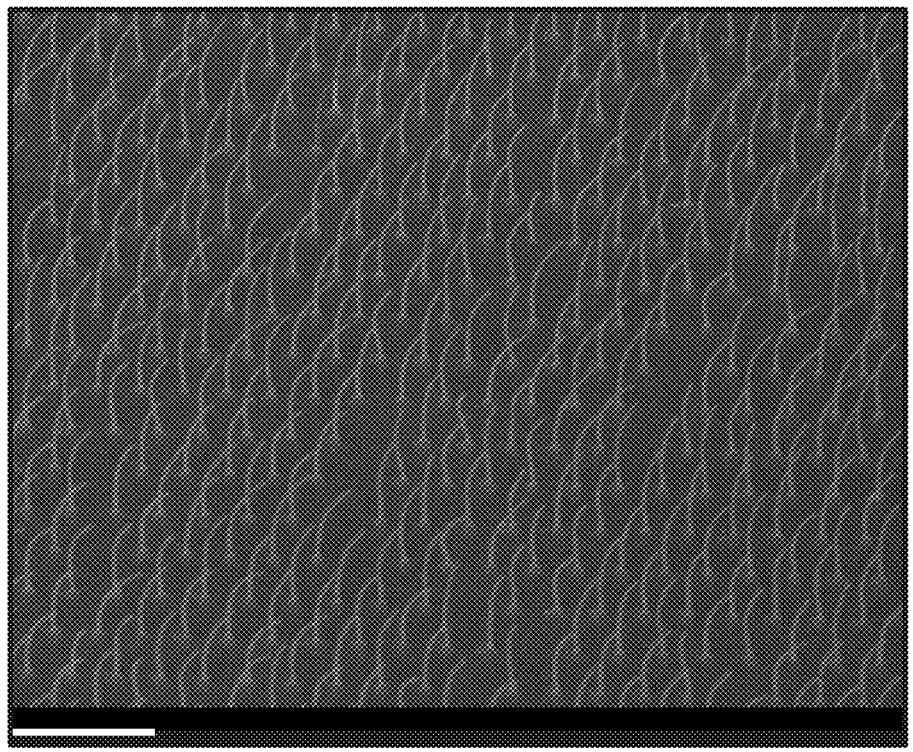
FIG. 9 is a SEM image of PVC nanofibers hot-embossed from a patterned laser-ablated nanopore mold. Scale bar is 20 μm.
Figure 10:
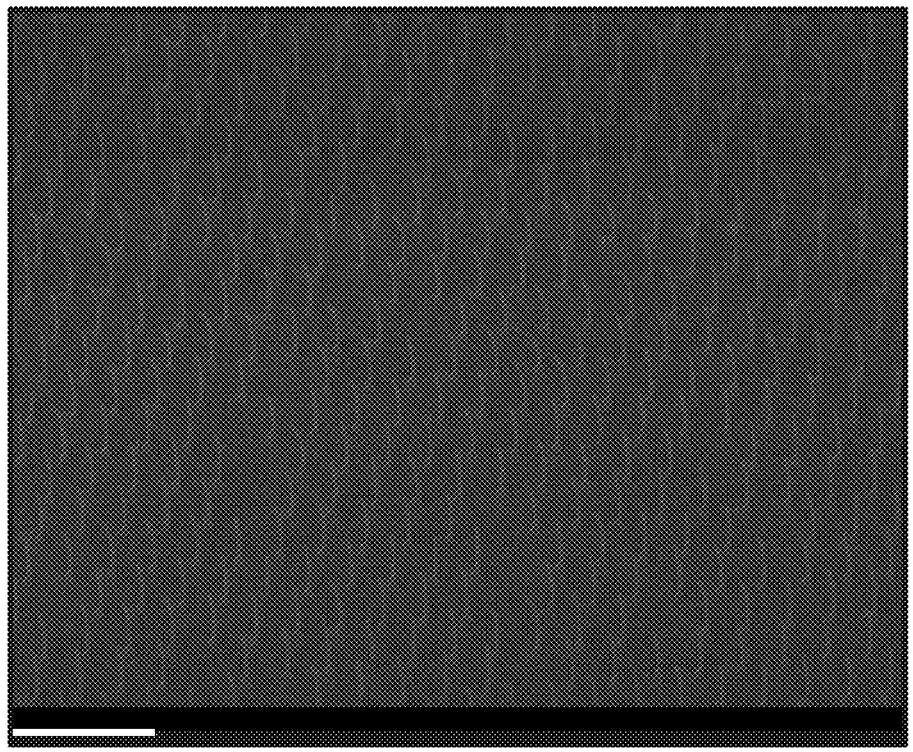
FIG. 10 is a SEM image of PVF nanofibers hot-embossed from a patterned laser-ablated nanopore mold. Scale bar is 20 μm.
Figure 11:
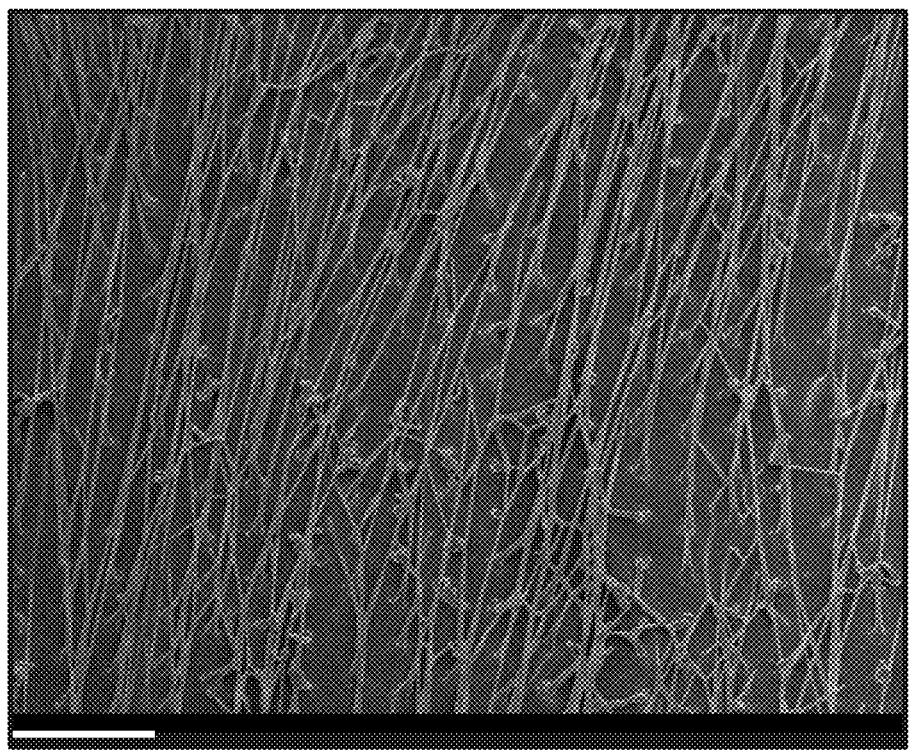
FIG. 11 is a SEM image of PI nanofibers hot-embossed from a patterned laser-ablated nanopore mold. Scale bar is 20 μm.
Figure 12:
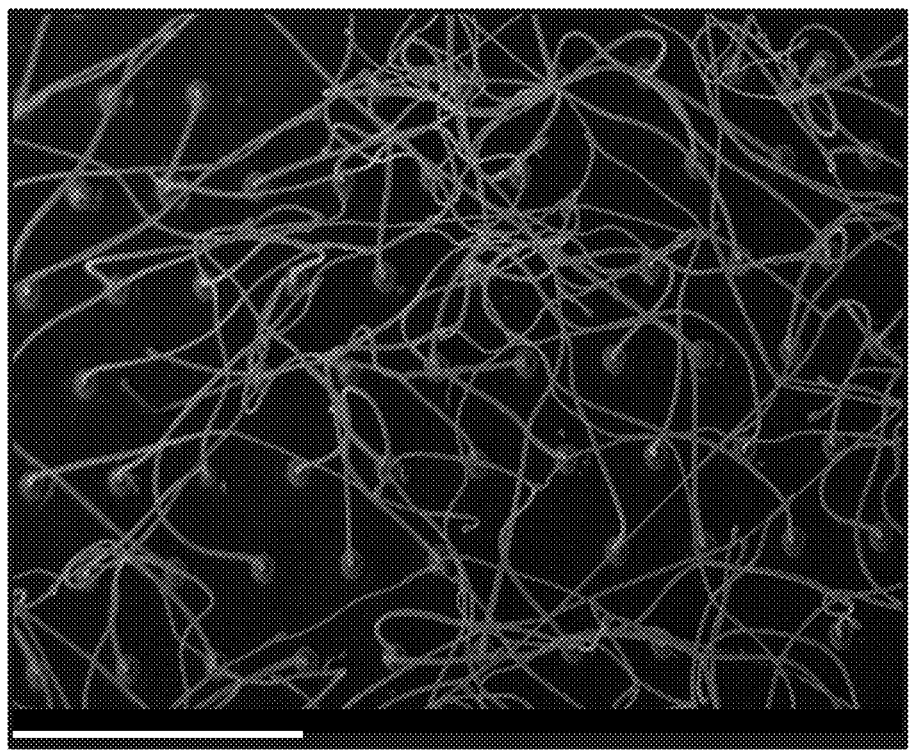
FIG. 12 is a SEM image of PP nanofibers hot-embossed from a patterned laser-ablated nanopore mold. Scale bar is 20 μm.
Figure 13:
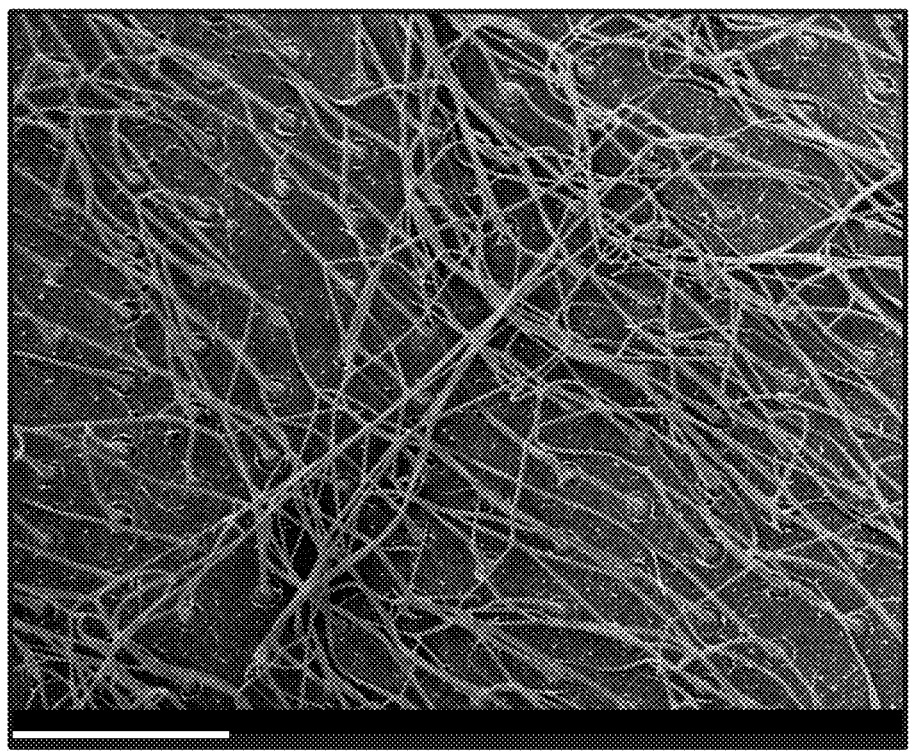
FIG. 13 is a SEM image of LDPE nanofibers hot-embossed from a patterned laser-ablated nanopore mold. Scale bar is 20 μm.
Figure 14:
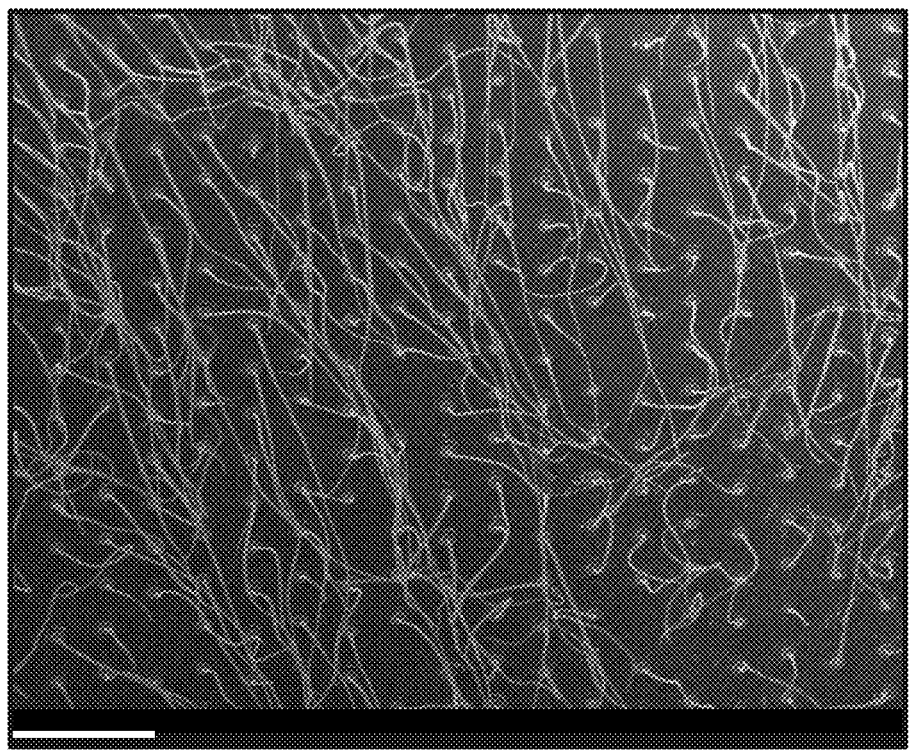
FIG. 14 is a SEM image of HDPE nanofibers hot-embossed from a patterned laser-ablated nanopore mold. Scale bar is 20 μm.
Figure 15:
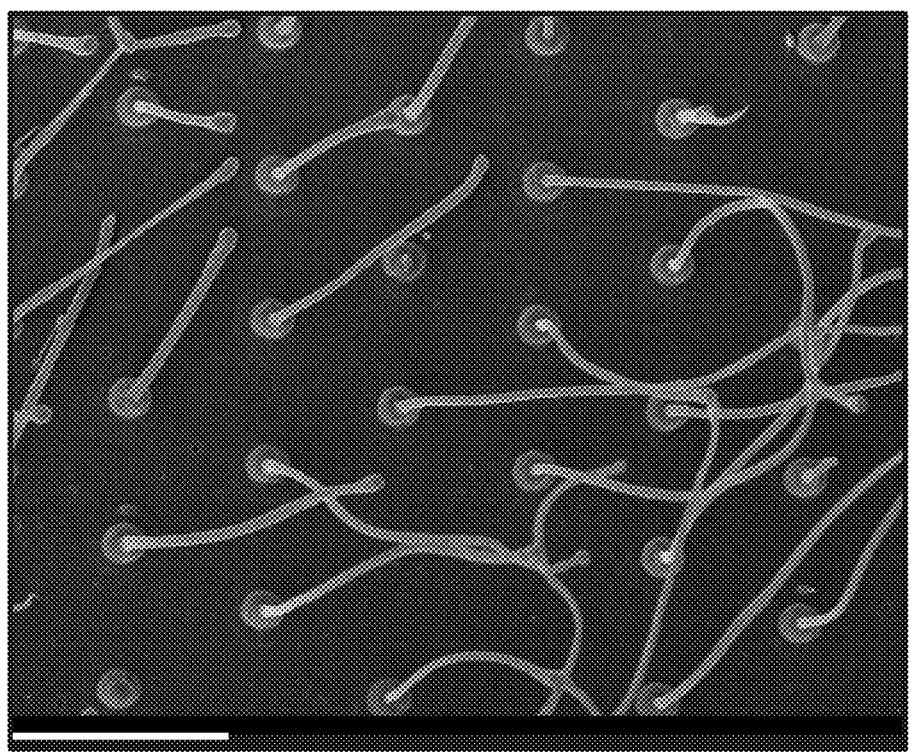
FIG. 15 is a SEM image of PiPc nanofibers hot-embossed from a patterned laser-ablated nanopore mold. Scale bar is 10 µm.
Figure 16:
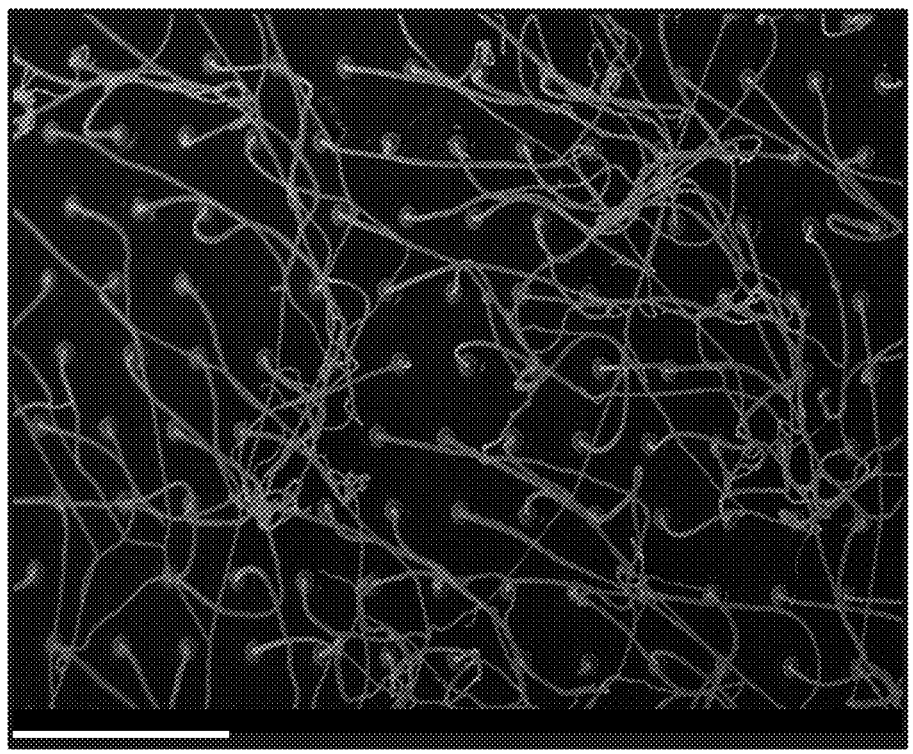
FIG. 16 is a SEM image of PiPn nanofibers hot-embossed from a patterned laser-ablated nanopore mold. Scale bar is 20 µm.
Figure 17:
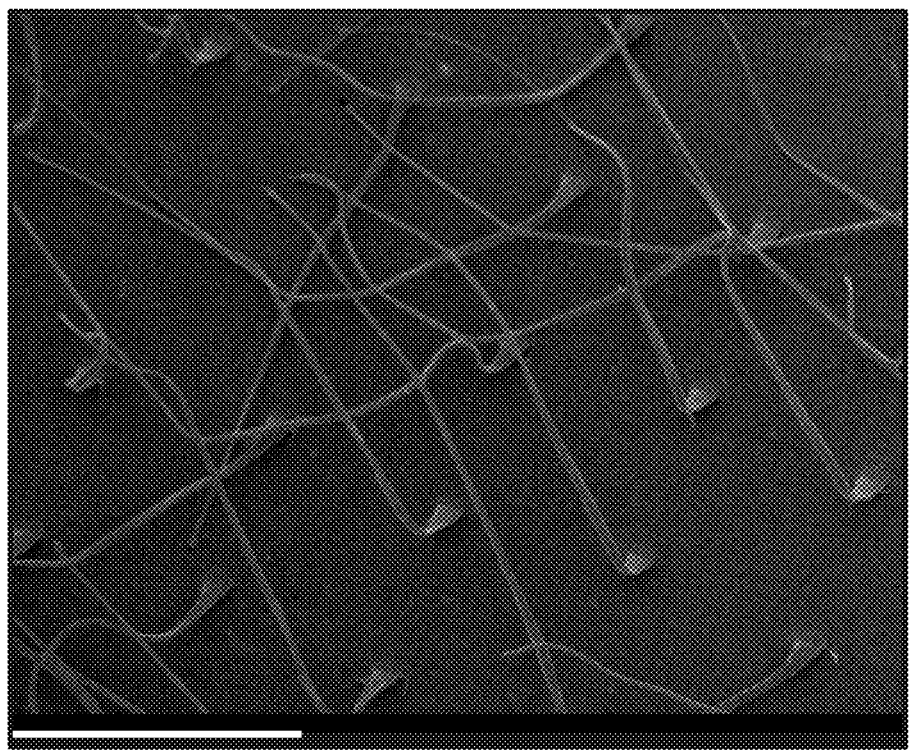
FIG. 17 is a SEM image of PVDF nanofibers hot-embossed from a patterned laser-ablated nanopore mold. Scale bar is 20 µm.

The technique of forming arrays of polymer nanofibers by hot-pressing thermoplastic polymers into patterned femtosecond laser-ablated nanopore molds using the hot-pressing system depicted in FIGS. 1A-B was successfully demonstrated for each of the polymers listed in Table 2, which provides the glass transition, $T_G$, and melting, $T_M$, temperatures of each polymer. The specific hot-pressing processing conditions used for each polymer and the average recorded pile height and length dimensions for nanofibers formed from these polymers are given in Table 3. All nanofibers were hot-pressed using the applicable temperature and pressure parameters listed in Table 3, and the temporal hold conditions given in the thermal cycle profile shown in FIG. 6, which were used for PI and PVC. Except for PVDF, all nanofibers were produced using the same laser-ablated nanopore mold. Hot-pressing hold temperatures were attained using an active PID controller. SEM images of nanofibers hot-pressed using the processing conditions listed in Table 3 are provided as FIGS. 7-17.

TABLE 2

Glass transition and melting temperatures of certain thermoplastic polymers.

| Material | $T_G$ (° C.) | $T_M$ (° C.) |
|---|---|---|
| Poly(ε-caprolactone) (PCL) | −60 | 60 |
| Polyethylene oxide (PEG) | −67 | 65 |
| Polyvinyl chloride (PVC) | 80 | 220 |
| Polyvinyl formal (PVF) | 105 | — |
| Polyisoprene, trans (PI) | −66 | 65 |
| Polypropylene (PP) | −20 | 160-175 |
| Low-density polyethylene (LDPE) | −110 | 115 |
| High-density polyethylene (HDPE) | −125 | 130 |

TABLE 2-continued

Glass transition and melting temperatures of certain thermoplastic polymers.

| Material | $T_G$ (° C.) | $T_M$ (° C.) |
|---|---|---|
| PIP Castline (PiPc) | — | — |
| PIP Natural (PiPn) | — | — |
| Polyvinylidene fluoride (PVDF) | −40 | 155-160 |

TABLE 3

Processing conditions and fiber length dimensions for thermoplastics successfully hot-pressed into nanofibers. Hold time = 5 minutes

| | Hot-Pressing Conditions | | | Nanofiber Dimensions | |
|---|---|---|---|---|---|
| Material | $T_{HOLD}$ (° C.) | $T_{QUENCH}$ (° C.) | Pressure (PSI) | Pile height Optical (um) | Length SEM (um) |
| PCL | 80 | 65 | 50 | 30 | 40 |
| PEG | 80 | 70 | 50 | 20 | 60 |
| PVC | 150 | 100 | 50 | 18 | 20 |
| PVF | 180 | 100 | 50 | 20 | 20 |
| PI | 150 | 100 | 50 | 20 | 60 |
| PP | 160 | 100 | 50 | 40 | 45 |
| LDPE | 140 | 100 | 50 | 30-40 | 60 |
| HDPE | 140 | 100 | 50 | 20 | 40 |
| PiPc | 140 | 100 | 50 | 20 | 25 |
| PiPn | 155 | 100 | 50 | 25 | 45 |
| PVDF | >180 | 100 | 50 | 20 | 55 |

The dependence of the hot-pressing process on temperature, applied pressure, and hold time were also investigated. Two distinct behaviors were observed regarding temperature dependence. First, it was observed that PCL only forms nanofibers if it reaches its melting temperature. Below the melting temperature, no nanofibers form. When PCL is held at or above its melting temperature, nanofibers at least 25 μm long will form. Second, PVC forms a nanopore mold-replicating pattern at temperatures slightly above its glass transition temperature. At 100° C., shallow (sub-micrometer tall) features are observed. As the temperature increases above 150° C., the height of these features increases progressively, up to 20 μm long. These behaviors are summarized in Table 4.

TABLE 4

Dependence of pattern replication on hold temperature. Hold time = 5 minutes.

| | Hot-Pressing Conditions | | | |
|---|---|---|---|---|
| Material | $T_{HOLD}$ (° C.) | $T_{QUENCH}$ (° C.) | Pressure (PSI) | Pattern Observation under Optical Microscope |
| PCL | 52-55 | 40 | 50 | No visible pattern |
| PCL | 53-57 | 40 | 50 | Faint and incomplete pattern |
| PCL | 56-59 | 40 | 50 | Complete pattern with 10-25 μm fibers |
| PVC | 100 | 90 | 50 | Complete pattern with <1 μm high features |
| PVC | 110 | 100 | 50 | Complete pattern with 1-2 μm high features |
| PVC | 120 | 100 | 50 | Complete pattern with 3 μm posts |
| PVC | 130 | 100 | 50 | Complete pattern with 4 μm posts |
| PVC | 140 | 100 | 50 | Complete pattern with 5 μm fibers |
| PVC | >150 | 100 | 50 | Complete pattern with 20 μm fibers |

For PVC, the hot-press hold time was observed to affect the height of the nanofibers produced. Data obtained using a hold temperature of 140° C. is presented in Table 5.

TABLE 5

Dependence of PVC nanofiber height on hot-press hold time

| Hot-Pressing Conditions | | | | Pattern |
|---|---|---|---|---|
| Hold time (s) | $T_{HOLD}$ (° C.) | $T_{QUENCH}$ (° C.) | Pressure (PSI) | Observation under Optical Microscope |
| 300 | 140 | 100 | 50 | 5 μm fibers |
| 600 | 140 | 100 | 50 | 9 μm fibers |
| 900 | 140 | 100 | 50 | 12 μm fibers |

Finally, it was observed that polymer nanofibers with heights in the tens-of-micrometers range can be formed with the application of only minimal (near pressure-less) pressure, as long as the hold temperature is high enough. This was observed for both PCL and PVC. Data obtained for these two materials is included in Table 6.

TABLE 6

Dependence of hot-pressing on applied pressure

| | Hot-Pressing Conditions | | | Pattern |
|---|---|---|---|---|
| Material | $T_{HOLD}$ (° C.) | $T_{QUENCH}$ (° C.) | Pressure (PSI) | Observation under Optical Microscope |
| PVC | 150 | 100 | <5 | 6 um fibers |
| PVC | 160 | 100 | <5 | 11-18 um fibers |
| PCL* | 80 | — | gravity | 35 um fibers |

*performed on a hot-plate rather than the hot-pressing system shown in FIGS. 1A-B.

This data indicates that for some polymers melting is not necessary to form polymer nanofibers in the patterned nanopore molds. As a thermoplastic warms above the glass transition temperature the viscosity decreases exponentially and at some point if the surface forces in the nanopore overcome the viscous forces in the polymer then the material flows into the hole. For a given thermoplastic polymer applied pressure need only be enough to ensure conformal contact between the polymer sheet and the template if the hold temperature is sufficiently high.

Conclusion

The present disclosure presents the fabrication and implementation of new polymer nanofiber cell culture substrates for hMSCs. The inventors demonstrated the tunability of the polymer nanofiber models by varying the template nanopore spacing and etch time. When hMSCs were cultured on these polymer nanofiber models compared to TCPS or flat PCL substrates, their stemness was significantly improved likely by promoting cell-cell over cell-matrix interactions. The inherent ability of the polymer models to promote contact guidance of hMSCs lead to large scale coordinated behavior and ultimately the formation of tissue like structures [41]. hMSCs were observed to interact directly with polymer fibers, which resulted in gross morphological differences between cells cultured on flat substrates. These morphological changes were accompanied by significant increases in expression of key self-renewal factors Nanog and OCT4A, as well as significantly increased expression of cell-cell interaction markers PECAM and ITGA2. Of the groups tested, the 2×3 polymer nanofibers showed the most drastic increases in stemness and cell-cell interactions. From this result, it is hypothesized that the increase in expression of self-renewal factors was mediated by increased cell-cell interaction that could only occur if the culture substrate embodied characteristics native to the bone marrow environment. Future studies utilizing these templates can work toward understanding the signaling mechanism linking increased cell-cell adhesion with increased stemness gene expression.

Taken together, the polymer nanofiber substrates disclosed herein serve as ECM mimetic substrates that can reinstate hMSC stemness. With increased expression of stemness and cell-cell marker genes, certain fiber arrangements promote a pseudo status of "forced aggregation" in hMSC culture. In contrast to traditional three-dimensional substrates, these polymer models provide drastic improvements in terms of consistency, ease of use, tunability, and scalability while at the same time providing one of the few culture substrate options that allow access to hMSCs that have not lost their stemness expression in in vitro culture.

The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Throughout this document, various references are mentioned. All such references are incorporated herein by reference, including the references set forth in the following list:

REFERENCES

1. Tibbitt M W, Anseth K S. Hydrogels as extracellular matrix mimics for 3D cell culture. Biotechnol Bioeng. 2009; 103(4):655-63.
2. Pathak A, Kumar S. Biophysical regulation of tumor cell invasion: moving beyond matrix stiffness. Integr Biol (Camb). 2011; 3(4):267-78.
3. Jahani H, Jalilian F A, Wu C Y, Kaviani S, Soleimani M, Abassi N, et al. Controlled surface morphology and hydrophilicity of polycaprolactone toward selective differentiation of mesenchymal stem cells to neural like cells. J Biomed Mater Res A. 2015; 103(5):1875-81.
4. Mohan N, Nair P D, Tabata Y. Growth factor-mediated effects on chondrogenic differentiation of mesenchymal stem cells in 3D semi-IPN poly(vinyl alcohol)-poly (caprolactone) scaffolds. J Biomed Mater Res A. 2010; 94(1):146-59.
5. Xue D, Zheng Q, Zong C, Li Q, Li H, Qian S, et al. Osteochondral repair using porous poly(lactide-co-glycolide)/nano-hydroxyapatite hybrid scaffolds with undifferentiated mesenchymal stem cells in a rat model. J Biomed Mater Res A. 2010; 94(1):259-70.
6. Lindstrom S, Iles A, Persson J, Hosseinkhani H, Hosseinkhani M, Khademhosseini A et al. Nanoporous Titania Coating of Microwell Chips for Stem Cell Culture and Analysis. J Biomech Sci Eng. 2010; 5(3)272-79.
7. Hosseinkhani H, Hiraoka Y, Li C H, Chen Y R, Yu D S, Hong P D, et al. Engineering three-dimensional collagen-IKVAV matrix to mimic neural microenvironment. ACS Chem Neurosci. 2013; 4(8):1229-35.
8. Tanabe S. Origin of cells and network information. World J Stem Cells. 2015; 7(3):535-40.

9. Bartosh T J, Ylostalo J H, Mohammadipoor A, Bazhanov N, Coble K, Claypool K, et al. Aggregation of human mesenchymal stromal cells (MSCs) into 3D spheroids enhances their antiinflammatory properties. Proc Natl Acad Sci USA. 2010; 107(31):13724-9.
10. Bara J J, Richards R G, Alini M, Stoddart M J. Concise review: Bone marrow-derived mesenchymal stem cells change phenotype following in vitro culture: implications for basic research and the clinic. Stem Cells. 2014; 32(7):1713-23.
11. Sart S, Tsai A C, Li Y, Ma T. Three-Dimensional Aggregates of Mesenchymal Stem Cells: Cellular Mechanisms, Biological Properties, and Applications. Tissue engineering Part B, Reviews. 2013.
12. Kinney M A, McDevitt T C. Emerging strategies for spatiotemporal control of stem cell fate and morphogenesis. Trends Biotechnol. 2013; 31(2):78-84.
13. Guvendiren M, Burdick J A. Engineering synthetic hydrogel microenvironments to instruct stem cells. Curr Opin Biotechnol. 2013; 24(5):841-6.
14. Nikkhah M, Edalat F, Manoucheri S, Khademhosseini A. Engineering microscale topographies to control the cell-substrate interface. Biomaterials. 2012; 33(21):5230-46.
15. Engler A J, Sen S, Sweeney H L, Discher D E. Matrix elasticity directs stem cell lineage specification. Cell. 2006; 126(4):677-89.
16. Heidemann S R, Wirtz D. Towards a regional approach to cell mechanics. Trends Cell Biol. 2004; 14(4):160-6.
17. Paszek M J, Zahir N, Johnson K R, Lakins J N, Rozenberg G I, Gefen A, et al. Tensional homeostasis and the malignant phenotype. Cancer Cell. 2005; 8(3):241-54.
18. Pelham Jr R J, Wang Y. Cell locomotion and focal adhesions are regulated by substrate flexibility. Proc Natl Acad Sci USA. 1997; 94(25):13661-5.
19. Foster C S, Smith C A, Dinsdale E A, Monaghan P, Neville A M. Human mammary gland morphogenesis in vitro: the growth and differentiation of normal breast epithelipmn collagen gel cultures defined by electron microscopy, monoclonal antibodies, and autoradiography. Dev Biol. 1983; 96(1):197-216.
20. Roeder B A, Kokini K, Sturgis J E, Robinson J P, Voytik-Harbin S L. Tensile mechanical properties of three-dimensional type I collagen extracellular matrices with varied microstructure. J Biomech Eng. 2002; 124(2):214-22.
21. Barcellos-Hoff M H, Aggeler J, Ram T G, Bissell M J. Functional differentiation and alveolar morphogenesis of primary mammary cultures on reconstituted basement membrane. Development. 1989; 105(2):223-35.
22. Kumar S. Cellular mechanotransduction: stiffness does matter. Nat Mater. 2014; 13(10):918-20.
23. Hockemeyer K, Janetopoulos C, Terekhov A, Hofmeister W, Vilgelm A, Costa L, et al. Engineered three-dimensional microfluidic device for interrogating cell-cell interactions in the tumor microenvironment. Biomicrofluidics. 2014; 8(4):044105.
24. Miroshnikova Y A, Jorgens D M, Spirio L, Auer M, Sarang-Sieminski A L, Weaver V M. Engineering strategies to recapitulate epithelial morphogenesis within synthetic three-dimensional extracellular matrix with tunable mechanical properties. Phys Biol. 2011; 8(2):026013.
25. Murphy W L, McDevitt T C, Engler A J. Materials as stem cell regulators. Nat Mater. 2014; 13(6):547-57.
26. McMurray R J, Gadegaard N, Tsimbouri P M, Burgess K V, McNamara L E, Tare R, et al. Nanoscale surfaces for the long-term maintenance of mesenchymal stem cell phenotype and multipotency. Nat Mater. 2011; 10(8):637-44.
27. Dubey N, Letourneau P C, Tranquillo R T. Neuronal contact guidance in magnetically aligned fibrin gels: effect of variation in gel mechano-structural properties. Biomaterials. 2001; 22(10): 1065-75.
28. McCall A S, Cummings C F, Bhave G, Vanacore R, Page-McCaw A, Hudson B G. Bromine Is an Essential Trace Element for Assembly of Collagen I V Scaffolds in Tissue Development and Architecture. Cell. 2014; 157(6):1380-92.
29. Rajput D, Costa L, Lansford K, Terekhov A, Hofmeister W. Solution-Cast High-Aspect-Ratio Polymer Structures from Direct-Write Templates. Acs Appl Mater Inter. 2013; 5(1):1-5.
30. White Y V, Li X X, Sikorski Z, Davis L M, Hofmeister W. Single-pulse ultrafast-laser machining of high aspect nano-holes at the surface of SiO2. Opt Express. 2008; 16(19):14411-20.
31. Bhuyan M K, Courvoisier F, Lacourt P A, Jacquot M, Salut R, Furfaro L, et al. High aspect ratio nanochannel machining using single shot femtosecond Bessel beams. Appl Phys Lett. 2010; 97(8):081102.
32. Courvoisier F, Lacourt P A, Jacquot M, Bhuyan M K, Furfaro L, Dudley J M. Surface nanoprocessing with nondiffracting femtosecond Bessel beams. Opt Lett. 2009; 34(20):3163-5.
33. Delobelle B, Salut R, Courvoisier F, Delobelle P. A detailed study through the focal region of near-threshold single-shot femtosecond laser ablation nano-holes in borosilicate glass. Opt Commun. 2011; 284:5746-57.
34. Herbstman J F, Hunt A J. High-aspect ratio nanochannel formation by single femtosecond laser pulses. Opt Express. 2010; 18(16):16840-8.
35. Chou C L, Rivera A L, Sakai T, Caplan A I, Goldberg V M, Welter J F, et al. Micrometer Scale Guidance of Mesenchymal Stem Cells to Form Structurally Oriented Cartilage Extracellular Matrix. Tissue Eng Pt A. 2013; 19(9-10):1081-90.
36. Mitsui K, Tokuzawa Y, Itoh H, Segawa K, Murakami M, Takahashi K, et al. The homeoprotein Nanog is required for maintenance of pluripotency in mouse epiblast and ES cells. Cell. 2003; 113(5):631-42.
37. Albelda S M, Muller W A, Buck C A, Newman P J. Molecular and Cellular Properties of Pecam-1 (Endocam/Cd31)—a Novel Vascular Cell Cell-Adhesion Molecule. J Cell Biol. 1991; 114(5):1059-68.
38. Deans R J, Moseley A B. Mesenchymal stem cells: Biology and potential clinical uses. Exp Hematol. 2000; 28(8):875-84.
39. Yu X, Miyamoto S, Mekada E. Integrin alpha 2 beta 1-dependent EGF receptor activation at cell-cell contact sites. J Cell Sci. 2000; 113(Pt 12):2139-47.
40. Sart S, Tsai A C, Li Y, Ma T. Three-dimensional aggregates of mesenchymal stem cells: cellular mechanisms, biological properties, and applications. Tissue Eng B Rev. 2014; 20(5):365-80.
41. Londono C, Loureiro M J, Slater B, Lucker P B, Soleas J, Sathananthan S, et al. Nonautonomous contact guidance signaling during collective cell migration. Proc Natl Acad Sci USA. 2014; 111(5):1807-12.

What is claimed is:

1. A method of manufacturing a cell culture substrate, consisting of:

providing a mold having a patterned array of nanopores laser ablated in a surface thereof;

pressing a thermoplastic polymer film against the surface of the mold;

heating the polymer film to a temperature greater than the melting temperature of the polymer;

allowing the polymer to melt and infiltrate the nanopores in the absence of a solvent;

cooling the melted polymer to a temperature below the melting temperature of the polymer until the melted polymer solidifies; and removing the solidified polymer from the mold as a cell culture substrate;

wherein the cell culture substrate comprises a plurality of freestanding polymer nanofibers integrally formed on a surface of the film along an X-axis and a Y-axis at the same or different intervals along either axis, the nanofibers having a length of at least 10 microns, a base portion that extends at least 1 micron outwardly from the surface of the film at an angle substantially perpendicular to the surface of the film, a tip opposite the base portion, and an average diameter between the base portion and the tip of from about 0.10 microns to about 1.20 microns.

* * * * *